United States Patent
Birkhold et al.

(10) Patent No.: US 11,786,203 B2
(45) Date of Patent: Oct. 17, 2023

(54) DETERMINING AN IMAGE DATASET

(71) Applicant: Siemens Healthcare GmbH, Erlangen (DE)

(72) Inventors: Annette Birkhold, Nuremberg (DE); Markus Kowarschik, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 852 days.

(21) Appl. No.: 16/743,038

(22) Filed: Jan. 15, 2020

(65) Prior Publication Data

US 2020/0237330 A1 Jul. 30, 2020

(30) Foreign Application Priority Data

Jan. 24, 2019 (DE) .......................... 102019200888.7

(51) Int. Cl.
*A61B 6/00* (2006.01)
*G06T 11/00* (2006.01)
*A61B 6/03* (2006.01)

(52) U.S. Cl.
CPC ............ *A61B 6/5205* (2013.01); *A61B 6/032* (2013.01); *G06T 11/006* (2013.01); *G06T 2210/41* (2013.01)

(58) Field of Classification Search
CPC ..... A61B 6/5205; A61B 6/032; G06T 11/006; G06T 2210/41
See application file for complete search history.

(56) References Cited

U.S. PATENT DOCUMENTS

| 5,396,418 A * | 3/1995 | Heuscher | G16H 20/17 378/15 |
| 8,963,919 B2 * | 2/2015 | Mistretta | A61B 6/032 382/131 |
| 10,165,997 B2 * | 1/2019 | Baumgart | A61B 6/504 |
| 11,317,875 B2 * | 5/2022 | Schafer | A61B 6/486 |
| 11,508,100 B2 * | 11/2022 | Kaethner | G06T 11/008 |

(Continued)

FOREIGN PATENT DOCUMENTS

| DE | 102012211472 A1 | 1/2014 |
| DE | 102015224176 A1 | 6/2017 |
| DE | 102017220489 A1 | 5/2019 |

*Primary Examiner* — Khai M Nguyen
(74) *Attorney, Agent, or Firm* — Harness, Dickey & Pierce, P.L.C.

(57) ABSTRACT

A method is for determining a three-dimensional image dataset. In an embodiment, the method includes a first X-ray dataset of the examination volume being received, the first X-ray dataset including a two-dimensional first X-ray projection of the examination volume with respect to a first projection direction; and a second X-ray dataset of the examination volume being received, the second X-ray dataset including a second two-dimensional X-ray projection of the examination volume with respect to a second projection direction. Furthermore, a first three-dimensional image dataset of the examination volume is determined based on the two-dimensional first X-ray projection and the two-dimensional second X-ray projection. An effect of overlaps of vessels with respect to the first projection direction or the second projection direction can be reduced as a result of determining the first three-dimensional image dataset based on the first X-ray dataset and the second X-ray dataset.

32 Claims, 11 Drawing Sheets

(56) References Cited

U.S. PATENT DOCUMENTS

| | | | |
|---|---|---|---|
| 2005/0046644 A1* | 3/2005 | Ohishi | G06T 11/005 345/643 |
| 2013/0237815 A1* | 9/2013 | Klingenbeck | A61B 6/4014 600/431 |
| 2016/0048959 A1* | 2/2016 | Kowarschik | G16H 50/30 600/425 |
| 2017/0249758 A1* | 8/2017 | Mistretta | A61B 6/4028 |
| 2018/0040147 A1* | 2/2018 | Alhrishy | A61B 6/5205 |
| 2018/0182132 A1* | 6/2018 | Kowarschik | A61B 6/504 |
| 2018/0199905 A1 | 7/2018 | Kowarschik et al. | |
| 2018/0368784 A1 | 12/2018 | Klingenbeck et al. | |
| 2020/0013153 A1* | 1/2020 | Kaethner | G06N 3/084 |

* cited by examiner

DETERMINING AN IMAGE DATASET

PRIORITY STATEMENT

The present application hereby claims priority under 35 U.S.C. § 119 to German patent application number DE 102019200888.7 filed Jan. 24, 2019, the entire contents of which are hereby incorporated herein by reference.

FIELD

Embodiments of the invention generally relate to a determination system or a computer-implemented method for determining a three-dimensional image dataset.

BACKGROUND

In digital subtraction angiography (DSA for short), one or more vessels are visualized by way of acquired X-ray images, the process entailing image acquisitions of the vessel alone being combined with image acquisitions of the vessel including a contrast agent that is present in the vessel in order to suppress further structures in the examination volume. With this technique, the contrast agent is introduced into the vessel during the examination in order to determine parameters, in particular hydrodynamic parameters of a fluid, while the fluid flows in the vessel.

In four-dimensional DSA, a temporally resolved series of three-dimensional DSA image data is provided by way of an image reconstruction method. In this case, normalized two-dimensional X-ray projections of an examination volume are backprojected together with time information into a volume element. The two-dimensional X-ray projections are typically derived here from a rotating acquisition protocol of a C-arm X-ray device.

Multiplicative back-projection is subject to constraints if multiple vessels or multiple vessel segments overlap in the two-dimensional X-ray projections. In this case it is not evident from a single X-ray projection to which of the overlapping vessels an X-ray signal, in particular an intensity value or an X-ray absorption coefficient, must be assigned.

SUMMARY

The inventors have discovered that although it is known to perform a spatial and/or a temporal interpolation in the case of overlapping vessels; the result of such an interpolation is imprecise and may deviate from the actual conditions within the examination volume.

At least one embodiment of the invention provides a solution to improve the accuracy of four-dimensional DSA, in particular when vessel overlaps are present.

Embodiments include a method for determining a three-dimensional image dataset, a determination system, a computer program product, and a computer-readable storage medium. Advantageous embodiments and developments as well as alternatives are disclosed in the claims and in the description. Also disclosed in particular are methods for determining a four-dimensional image dataset. These are to be understood in particular as an extension or as a multiple execution of the method for determining a three-dimensional image dataset.

Embodiments are described below both in relation to devices and methods. Features, advantages or alternative embodiment variants mentioned herein are equally to be applied also to the other claimed objects, and vice versa. In other words, the object-related claims (which are directed for example to a device) can also be developed by way of the features that are described or claimed in connection with a method. The corresponding functional features of the method are in this case embodied by way of corresponding object-related modules.

At least one embodiment of the invention relates, in a first aspect, to a computer-implemented method for determining a three-dimensional image dataset. The method is based on the premise that a first X-ray dataset of the examination volume is received, the first X-ray dataset comprising a first two-dimensional X-ray projection of the examination volume with respect to a first projection direction. In addition, a second X-ray dataset of the examination volume is received, the second X-ray dataset comprising a second two-dimensional X-ray projection of the examination volume with respect to a second projection direction. Furthermore, a first three-dimensional image dataset of the examination volume is determined based on the first X-ray projection and the second X-ray projection. Optionally, the first three-dimensional image dataset is provided, in which case the provision of the first three-dimensional image dataset may comprise in particular a storing, a transmission and/or a displaying of the three-dimensional image dataset.

An embodiment of the invention may furthermore relates to a computer-implemented method for determining a four-dimensional image dataset, comprising a receiving of first X-ray datasets of an examination volume, wherein each X-ray dataset of the first X-ray datasets comprises a two-dimensional X-ray projection of the examination volume with respect to a projection direction, as well as, in addition, a receiving of second X-ray datasets of the examination volume, wherein each X-ray dataset of the second X-ray datasets comprises a two-dimensional X-ray projection of the examination volume with respect to a projection direction. The method further comprises a determining of a four-dimensional image dataset based on the first X-ray datasets and the second X-ray datasets. Optionally, the four-dimensional image dataset is provided, in which case the provision of the four-dimensional image dataset may comprise in particular a storing, a transmission and/or a displaying of the three-dimensional image dataset.

An embodiment of the invention also relates to a determination system for determining an image dataset of an examination volume, comprising an interface embodied for receiving a first X-ray dataset of the examination volume, wherein the first X-ray dataset comprises a two-dimensional first X-ray projection of the examination volume with respect to a first projection direction, further embodied for receiving a second X-ray dataset of the examination volume, wherein the second X-ray dataset comprises a two-dimensional second X-ray projection of the examination volume with respect to a second projection direction; and a computing unit embodied for determining a first three-dimensional image dataset of the examination volume based on the first X-ray projection and the second X-ray projection.

An embodiment of the invention may also relate to a determination system for determining an image dataset of an examination volume, comprising an interface embodied for receiving a first X-ray dataset of the examination volume, wherein the first X-ray dataset comprises a two-dimensional first X-ray projection of the examination volume with respect to a first projection direction, further embodied for receiving a second X-ray dataset of the examination volume, wherein the second X-ray dataset comprises a two-dimensional second X-ray projection of the examination volume with respect to a second projection direction, further embodied for receiving a third X-ray dataset of the examination volume, wherein the third X-ray dataset comprises a two-dimensional third X-ray projection of the examination volume with respect to a third projection direction; and a computing unit embodied for determining a first three-dimensional image dataset of the examination volume based on the first X-ray projection and the second X-ray projection, further embodied for determining a second three-dimensional image dataset of the examination volume based on the second X-ray projection and the third X-ray projection.

The invention may also relate to a determination system for determining a four-dimensional image dataset of an examination volume, comprising:

an interface embodied for receiving first X-ray datasets of the examination volume, wherein each X-ray dataset of the first X-ray datasets comprises a two-dimensional X-ray projection of the examination volume with respect to a projection direction, further embodied for receiving second X-ray datasets of the examination volume, wherein each X-ray dataset of the second X-ray datasets comprises a two-dimensional X-ray projection of the examination volume with respect to a projection direction; and a computing unit embodied for determining a four-dimensional image dataset based on the first X-ray datasets and the second X-ray datasets.

These determination systems may be embodied in particular for performing the above-described embodiments of inventive methods and their aspects. A determination system is embodied to perform these methods and their aspects, while the interface and/or the computing unit are embodied to perform the corresponding method steps.

An embodiment of the invention also relates to an X-ray device comprising one of the described determination systems. The X-ray device may in particular comprise a first X-ray source and a first X-ray detector. In addition, the X-ray device may in particular also comprise a second X-ray source and a second X-ray detector. The X-ray device may in particular be a C-arm X-ray device, a computed tomography system or a multisource X-ray device.

An embodiment of the invention also relates to computer program products comprising a computer program and a computer-readable medium. A largely software-based implementation has the advantage that determination systems already in use can also be easily upgraded by way of a software update in order to operate in the manner according to embodiments of the invention. As well as the computer program, such a computer program product may where applicable comprise additional constituent parts such as e.g. a set of documentation and/or additional components, including hardware components, such as e.g. hardware keys (dongles, etc.) to enable use of the software.

An embodiment is directed to a computer-implemented method for determining a three-dimensional image dataset of the examination volume, comprising:

receiving a first X-ray dataset of an examination volume, wherein the first X-ray dataset comprises a two-dimensional first X-ray projection of the examination volume with respect to a first projection direction, receiving a second X-ray dataset of the examination volume, wherein the second X-ray dataset comprises a two-dimensional second X-ray projection of the examination volume with respect to a second projection direction, determining a first three-dimensional image dataset of the examination volume based on the first X-ray projection and the second X-ray projection.

An embodiment is directed to a determination system to determine a three-dimensional image dataset of an examination volume, comprising:

an interface embodied to
receive a first X-ray dataset of the examination volume, the first X-ray dataset including a two-dimensional first X-ray projection of the examination volume with respect to a first projection direction,
receive a second X-ray dataset of the examination volume, the second X-ray dataset including a two-dimensional second X-ray projection of the examination volume with respect to a second projection direction; and a computing unit embodied to determine a first three-dimensional image dataset of the examination volume based on the two-dimensional first X-ray projection and the two-dimensional second X-ray projection.

An embodiment is directed to a non-transitory computer program product storing a computer program, directly loadable into a memory of a determination system, including program sections for performing the method of an embodiment when the program sections are executed by the determination system.

An embodiment is directed to a non-transitory computer-readable storage medium storing program sections, readable and executable by a determination system, to perform the method of an embodiment when the program sections are executed by the determination system.

BRIEF DESCRIPTION OF THE DRAWINGS

The above-described characteristics, features and advantages of this application, as well as the manner in which they are realized, will become clearer and more readily understandable in connection with the following description of the example embodiments, which are explained in more detail with reference to the drawings. This description implies no limitation of the invention to these example embodiments. Like components are labeled with identical reference signs in different figures. The figures are generally not to scale.

In the figures.

DETAILED DESCRIPTION OF THE EXAMPLE EMBODIMENTS

Figure 1:
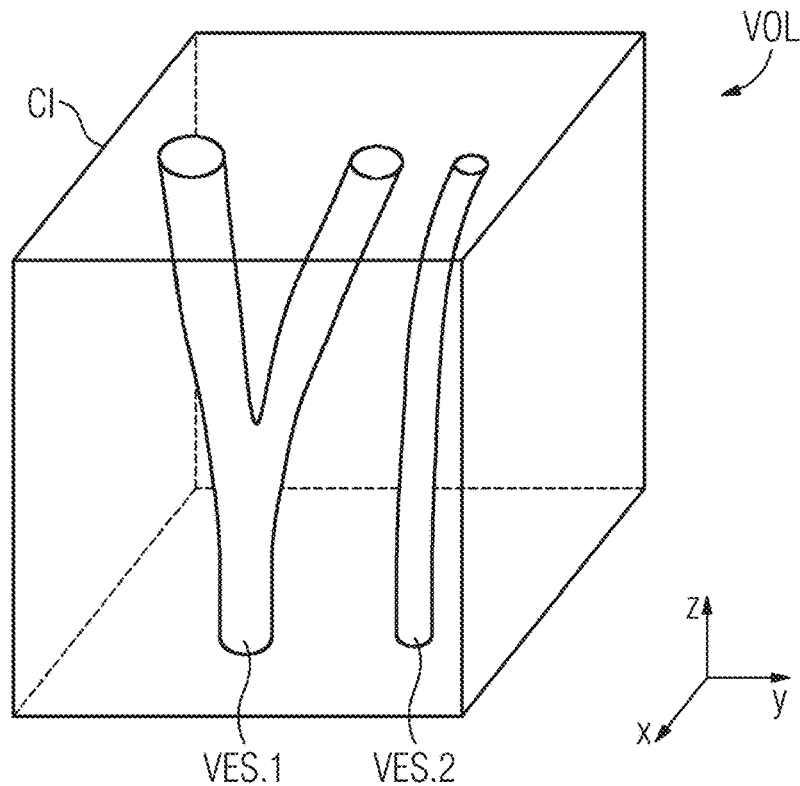
FIG. 1 shows an examination volume containing two vessels.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates, in a first aspect, to a computer-implemented method for determining a three-dimensional image dataset. The method is based on the premise that a first X-ray dataset of the examination volume is received, the first X-ray dataset comprising a first two-dimensional X-ray projection of the examination volume with respect to a first projection direction. In addition, a second X-ray dataset of the examination volume is received, the second X-ray dataset comprising a second two-dimensional X-ray projection of the examination volume with respect to a second projection direction. Furthermore, a first three-dimensional image dataset of the examination volume is determined based on the first X-ray projection and the second X-ray projection. Optionally, the first three-dimensional image dataset is provided, in which case the provision of the first three-dimensional image dataset may comprise in particular a storing, a transmission and/or a displaying of the three-dimensional image dataset.

The three-dimensional image dataset may in this case visualize in particular the condition of the examination volume, in particular the distribution of contrast agent in the examination volume, at a time coordinate. Furthermore, the three-dimensional image dataset may be in particular a part of a four-dimensional (spatially three-dimensional and temporally one-dimensional) image dataset that corresponds to a constant time coordinate.

The first X-ray dataset is received in particular via an interface. The second X-ray dataset is received in particular via the interface. The first three-dimensional image dataset is determined in particular via a computing unit. The optional provision of the first three-dimensional image dataset is accomplished in particular via the interface. The interface and the computing unit are in this case in particular component parts of a provider system.

An X-ray dataset is in particular a dataset comprising an X-ray projection, in particular comprising precisely one X-ray projection. As well as the X-ray projection, the X-ray dataset may also comprise in particular further data, for example the acquisition time point of the X-ray projection, the projection direction of the X-ray projection, the X-ray energy used for the X-ray projection, or characteristics of the X-ray source and/or the X-ray detector. Furthermore, the X-ray dataset may also include information concerning the examination volume, in particular concerning a patient.

An X-ray projection is a two-dimensional projection of an examination volume via X-ray beams along a projection direction which can in particular comprise a plurality of pixels. Each pixel is in this case assigned an X-ray intensity value which is a measure for the X-ray intensity incident in said pixel. The incident X-ray intensity is dependent on the number, the size, the shape and the material of the objects present in the examination volume, in particular on the spatial distribution of the X-ray absorption coefficient in the examination volume. A two-dimensional X-ray projection is in particular spatially two-dimensional.

An X-ray projection of the examination volume may in particular be based on further X-ray projections, in particular on a mask X-ray projection and a fill X-ray projection. The further X-ray projections, i.e. in particular the mask X-ray projection and the fill X-ray projection, may have been acquired in particular with respect to the same projection direction, but in particular at different time points. (The time point of the acquisition of the X-ray projection may then in particular be the time point of the acquisition of the fill X-ray projection).

The condition of the examination volume may vary in this case in particular between the acquisitions of the further X-ray projections. In particular, the examination volume may exhibit a different contrast agent distribution or contrast agent concentration during the acquisition of one of the further X-ray projections than during the acquisition of another of the further X-ray projections. In particular, the examination volume may contain no contrast agent during the acquisition of the mask X-ray projection, and the examination volume may contain contrast agent during the acquisition of the fill X-ray projection.

The X-ray projection can then in particular be a difference between the fill X-ray projection and the mask X-ray projection. The X-ray projection is then in particular a DSA X-ray projection (DSA being an acronym for "Digital Subtraction Angiography"). In a DSA X-ray projection, in particular structures which have not changed between the acquisition of the mask X-ray projection and the fill X-ray projection are not visualized or, as the case may be, are suppressed.

The terms "X-ray dataset" and "X-ray projection" may also be interchanged where this is deemed appropriate by the person skilled in the art. In particular, a statement concerning an X-ray dataset may also relate to the X-ray projection contained in the X-ray dataset, and a statement concerning an X-ray projection may relate to the X-ray dataset of which it is part.

The projection direction of an X-ray projection corresponds in particular to the direction between the X-ray source and the X-ray detector by which the X-ray projection is acquired at the time point of the acquisition of the X-ray projection. The projection direction may in particular be construed as a vector or as a straight line (defined by receiving point and direction vector) from the X-ray source to the X-ray detector. If the X-ray detector is embodied as a planar X-ray detector, the projection direction is in particular orthogonal to the X-ray detector.

An image dataset comprises multiple pixels or voxels, in particular a regular arrangement of pixels or voxels. An image dataset is in particular n-dimensional when it comprises an n-dimensional regular arrangement of pixels or voxels. In particular, an image dataset is two-dimensional, three-dimensional or four-dimensional. A two-dimensional image dataset is in particular spatially two-dimensional, a three-dimensional image dataset is in particular spatially three-dimensional, and a four-dimensional image dataset is in particular spatially three-dimensional and temporally one-dimensional. An n-dimensional regular arrangement of pixels or voxels is in particular an n-dimensional matrix.

In particular, the pixels or voxels of the image dataset are assigned one or more intensity values. The intensity values correspond in this case in particular to physical properties in an examination volume, e.g. to an X-ray absorption coefficient at a spatial position of the examination volume.

As well as the pixels or voxels, an image dataset may also comprise further data, for example the acquisition time point of the image dataset, the X-ray energy used during the acquisition of the image dataset, or characteristics of the device that acquired the image dataset. Furthermore, the image dataset may also comprise information concerning the examination volume, in particular concerning a patient. The image dataset may be in particular an image dataset conforming to the DICOM format (DICOM being an acronym for "Digital Imaging and Communications in Medicine").

In the following, an image dataset may be referred to as a real image dataset when it maps the actual distribution of values and/or intensities (e.g. Hounsfield units, X-ray attenuation coefficients) in an examination volume. An image dataset may be referred to as a difference image dataset when it maps a difference of an actual distribution of values and/or intensities in an examination volume. However, a difference image dataset is not necessarily determined by subtraction of two real image datasets. An image dataset may be referred to as a subtraction image dataset when it has been determined by subtraction of two image datasets, in particular by subtraction of two real image datasets. Every subtraction image dataset could therefore be construed in particular as a difference image dataset, but not every difference image dataset may be referred to as a subtraction image dataset.

The inventors have recognized that the effect of vessel overlaps with respect to the first projection direction or the second projection direction can be reduced as a result of determining the first three-dimensional image dataset based on the first X-ray dataset and the second X-ray dataset, and therefore the accuracy or the robustness of the first three-dimensional image dataset can be improved. In particular, vessels overlapping with respect to a first projection along the first projection direction cannot overlap with respect to a second projection along the second projection direction, and vice versa. The information lacking in the first projection as to which of the overlapping vessels an X-ray projection may be assigned can then be determined from the second projection, and vice versa.

According to a further aspect of an embodiment of the invention, the first projection direction and the second projection direction include an angle between 45° and 135°, in particular an angle between 60° and 120°, in particular an angle between 80° and 100°, in particular an angle between 85° and 95°. In particular, the first projection direction and the second projection direction are orthogonal.

If the first projection direction and the second projection direction are given by a vector in each case, in particular the angle between the first projection direction and the second projection direction corresponds to the angle between the vector of the first projection direction and the vector of the second projection direction. An angle between two projection directions can assume values between 0 and 180° (in degrees) or between 0 and $\pi$ (in radians). In particular, the angle $\varphi$ between a first vector $v_1$ and a second vector $v_2$ is given by $\cos(\varphi) = v_1 \circ v_2 / |v_1| |v_2|$, where $v_1 \circ v_2$ denotes the scalar product of the vectors $v_1$ and $v_2$, and where $|v_1|$ and $|v_2|$ denote the length of the vectors $v_1$ and $v_2$, respectively.

The inventors have recognized that as a result of this choice of the angle between the first and the second projection direction close to orthogonality, an overlap of vessels with respect to the first X-ray projection can be particularly well resolved by the second X-ray projection, and vice versa.

According to a further aspect of an embodiment of the invention, the first X-ray dataset comprises a first time point, the first time point corresponding to the time point of the acquisition of the first X-ray projection. Furthermore, the second X-ray dataset comprises a second time point, the second time point corresponding to the time point of the acquisition of the second X-ray projection. Furthermore, the time interval between the first time point and the second time point is less than 5 s, in particular less than 2 s, in particular less than 1 s, in particular less than 0.5 s, in particular less than 0.1 s, in particular less than 0.02 s. In particular, the first time point and the second time point may be identical.

If the first time point and the second time point are identical, the effects of scattered radiation must be corrected during the acquisition or processing of the first X-ray projection and the second X-ray projection by the acquisition of the other X-ray projection in each case.

If the three-dimensional image dataset has a time coordinate, then the value of the time coordinate can lie in particular between the first time point and the second time point.

The inventors have recognized that owing to the short time interval between the first and the second X-ray projection, only minor changes are produced in the examination volume, in particular with respect to the contrast agent concentration. Only minor artifacts are therefore produced in the first image dataset due to changes in the examination volume in the time between the acquisitions of the two X-ray projections.

According to a further aspect of an embodiment of the invention, the method for determining a three-dimensional image dataset further relates to a receiving of a third X-ray dataset of the examination volume, the third X-ray dataset comprising a two-dimensional third X-ray projection of the examination volume with respect to a third projection direction. The method further comprises a determining of a second three-dimensional image dataset of the examination volume based on the second X-ray projection and the third X-ray projection. Optionally, the second three-dimensional image dataset is provided, in which case the provision of the second three-dimensional image dataset may comprise in particular a storing, a transmission and/or a displaying of the second three-dimensional image dataset.

The third X-ray dataset is received in particular via the interface. The second three-dimensional image dataset is determined in particular via the computing unit. The optional provision of the first three-dimensional image dataset is accomplished in particular via the interface. The interface and the computing unit are in this case in particular component parts of the provider system.

Advantages described in relation to (the determining of) the first three-dimensional image dataset are realized in relation to (the determining of) the second three-dimensional image dataset. The inventors have furthermore recognized that as a result of using the second X-ray dataset both for determining the first three-dimensional image dataset and for determining the second three-dimensional image dataset, the X-ray dose or radiation dose can be reduced in the examination volume (in particular compared to the use of two separate X-ray datasets for the second three-dimensional image dataset).

According to a further aspect of an embodiment of the invention, the first projection direction and the second projection direction include an angle between 45° and 135°, in particular an angle between 60° and 120°, in particular an angle between 80° and 100°, in particular an angle between 85° and 95°. Furthermore, the second projection direction and the third projection direction include an angle between 45° and 135°, in particular an angle between 60° and 120°, in particular an angle between 80° and 100°, in particular an angle between 85° and 95°.

The inventors have recognized that as a result of this choice of the angle between the first, the second and the third projection direction close to orthogonality, an overlap of vessels with respect to the first X-ray projection can be particularly well resolved by the second X-ray projection, and vice versa.

According to a further aspect of an embodiment of the invention, the first projection direction and the third projection direction include an angle of less than 45°, in particular an angle of less than 30°, in particular an angle of less than 10°, in particular an angle of less than 5°.

The inventors have recognized that owing to the described small angle, an X-ray source and an X-ray detector which acquire the first and the third X-ray dataset must be moved only slightly between the acquisition of the first and the third X-ray dataset. As a result, in particular a faster acquisition sequence is possible for the respective X-ray projections.

According to a further aspect of an embodiment of the invention, the second X-ray dataset comprises a second time point, the second time point corresponding to the time point of the acquisition of the second X-ray projection. In addition, the third X-ray dataset comprises a third time point, the third time point corresponding to the time point of the acquisition of the third X-ray projection. Furthermore, the time interval between the second time point and the third time point is less than 5 s, in particular less than 2 s, in particular less than 1 s, in particular less than 0.5 s, in particular less than 0.1 s, in particular less than 0.02 s.

The inventors have recognized that owing to the short time interval between the second and the third X-ray projection, only minor changes are produced in the examination volume, in particular in relation to the contrast agent concentration. Only minor artifacts are therefore produced in the second image dataset due to changes in the examination volume in the time between the acquisitions of the two X-ray projections.

According to a further possible aspect of an embodiment of the invention, the first X-ray dataset also comprises a first time point, the first time point corresponding to the time point of the acquisition of the first X-ray projection. Furthermore, the second time point corresponds to the midpoint in time between the first time point and the third time point.

The inventors have recognized that owing to the choice of the second time point as the midpoint in time between the first time point and the third time point, the time interval between the first and the second time point corresponds to the time interval between the second and the third time point. As a result, the first and the second three-dimensional image dataset exhibit artifacts due to changes in the examination volume to the same extent, i.e. are therefore comparable in particular with regard to artifacts of said type. In particular, this advantageously enables the first and the second three-dimensional image dataset to be combined in a four-dimensional image dataset.

According to a further aspect of an embodiment of the invention, the method for determining a three-dimensional image dataset additionally comprises a determining of a three-dimensional constraining image dataset of the examination volume, the determining of the first three-dimensional image dataset additionally being based on the constraining image dataset. Optionally, the determining of the second three-dimensional image dataset is furthermore also based on the constraining image dataset. The constraining image dataset may in particular also be determined through the receiving of the constraining image dataset. The constraining image dataset is determined in particular via the computing unit and/or the interface.

A constraining image dataset is in particular an image dataset intended to highlight a structure, in particular vessels in the examination volume. In particular, the constraining image dataset can assign first values to pixels or voxels corresponding to the structure or vessels, and second values to the pixels or voxels not corresponding to the structure or vessels, the first and the second values being different. In particular, all first values may be identical, and in particular all second values may be identical. In particular, the constraining image dataset may be a binary image dataset, i.e. only one value of two possible values may be assigned to a pixel or voxel. A constraining image dataset may be used in particular to determine a four-dimensional DSA dataset, i.e. a dataset which describes the variation with time of a three-dimensional contrast agent concentration in the examination volume, by back-projection of individual X-ray projections.

The inventors have recognized that structures in the examination volume outside of the vessels to be examined (for example bones, soft tissue structures, implants) can be masked out of the first or second three-dimensional image dataset through the use of a constraining image dataset.

According to a further aspect of an embodiment of the invention, the determining of the constraining image dataset is based on the first X-ray dataset and the second X-ray dataset. Optionally, the determining of the constraining image dataset is additionally based on the third X-ray dataset.

In particular, one of the methods described in the unpublished European patent application 18182251.1, the entire contents of which are hereby incorporated herein by reference, or one of the methods described in the unpublished German patent applications 102019200270.6 and 102019200269.2, the entire contents of each of which are hereby incorporated herein by reference, may be used for determining the constraining image dataset. In this case, difference image datasets of the examination volume are generated without additional mask acquisitions.

In addition, however, it is also possible to determine a reconstruction based on the first X-ray dataset and on the second X-ray dataset (optionally also on the third X-ray dataset), and in particular also based on further X-ray datasets of the examination volume, and the constraining image dataset can be determined from the reconstructed image dataset by way of a segmentation, in particular a threshold value segmentation.

The inventors have recognized that by this, the determining of the three-dimensional image dataset can be performed in a self-consistent manner. In particular, the method is consequently not reliant on the constraining image dataset as input value.

According to a further aspect of an embodiment of the invention, the method for determining a three-dimensional image dataset additionally comprises a determining of a first three-dimensional back-projection dataset based on the first X-ray dataset and on the constraining image dataset, as well as a determining of a second three-dimensional back-projection dataset based on the second X-ray dataset and on the constraining image dataset. In this case, the first three-dimensional image dataset is based on the first three-dimensional back-projection dataset and on the second three-dimensional back-projection dataset.

According to a further possible aspect of an embodiment of the invention, the method for determining a three-dimensional image dataset additionally comprises a determining of a third three-dimensional back-projection dataset based on the third X-ray dataset and on the constraining image dataset. In this case, the second three-dimensional image dataset is based on the second three-dimensional back-projection dataset and on the third three-dimensional back-projection dataset.

The first back-projection dataset and the second back-projection dataset are determined in particular via the computing unit. The optional determination of the third back-projection dataset is in particular likewise carried out via the computing unit.

A back-projection dataset is in particular an m-dimensional image dataset that is based on a constraining image dataset and an n-dimensional image dataset, where n<m. In particular, the back-projection dataset is a back-projection of the n-dimensional image dataset onto the constraining image dataset, in particular a multiplicative back-projection. In particular, n=m−1 applies.

The inventors have recognized that an approximation of a three-dimensional reconstruction can be realized particularly easily by way of a back-projection of a two-dimensional X-ray projection onto a three-dimensional constraining image dataset (resulting in a three-dimensional back-projection dataset). By using a first and a second back-projection dataset it is simultaneously possible to take advantage of the fact that overlaps of vessels with respect to the first projection do not regularly occur in the second projection, and vice versa.

According to a further aspect of an embodiment of the invention, the determining of the first three-dimensional image dataset comprises a multiplication of the first back-projection dataset with the second back-projection dataset. In particular, the first three-dimensional image dataset is based on the result of the multiplication of the first back-projection dataset with the second back-projection dataset or, as the case may be, is identical with the result. A multiplication is in particular a pixel-wise or voxel-wise multiplication.

According to a further possible aspect of an embodiment of the invention, the determining of the second three-dimensional image dataset comprises a multiplication of the second back-projection dataset with the third back-projection dataset. In particular, the second three-dimensional image dataset is based on the result of the multiplication of the second back-projection dataset with the third back-projection dataset or, as the case may be, is identical with the result. A multiplication is in particular a pixel-wise or voxel-wise multiplication.

The inventors have recognized that a particularly good approximation of a three-dimensional reconstruction of the examination volume can be achieved based on the multiplication of two back-projection datasets.

According to a further aspect of an embodiment of the invention, the method for determining a three-dimensional image dataset additionally comprises an acquisition of the first X-ray dataset via a first X-ray source and a first X-ray detector of an X-ray device, as well as an acquisition of the second X-ray dataset via a second X-ray source and a second X-ray detector of the X-ray device. Optionally, the method additionally comprises an acquisition of the third X-ray dataset via the first X-ray source and the first X-ray detector. The first X-ray source and the second X-ray source may in particular be different X-ray sources of a multisource X-ray device. The first X-ray detector and the second X-ray detector may in particular be different X-ray detectors of the multisource X-ray device.

The inventors have recognized that by using a first and a second X-ray source or, as the case may be, a first and a second X-ray detector it is possible to choose a particularly small time interval between the acquisition of the first and the second X-ray dataset or, as the case may be, between the acquisition of the second and the third X-ray dataset, since the first X-ray source and the first X-ray detector or, as the case may be, the second X-ray source and the second X-ray detector can be arranged such that the angle between the optical axes virtually corresponds to the angle between the first and the second projection direction or, as the case may be, the angle between the second and the third projection direction. As a result, the time interval is no longer substantially determined by the mechanical movability of X-ray source and X-ray detector, but by the electronic control of X-ray sources and X-ray detectors or, as the case may be, by the physical properties of the respective sources of scattered radiation.

According to a further aspect of an embodiment of the invention, the method for determining a three-dimensional image dataset additionally comprises an acquisition of the first X-ray dataset via a first X-ray source and a first X-ray detector of an X-ray device, a first rotation of the first X-ray detector and the first X-ray source around the examination volume, as well as an acquisition of the second X-ray dataset via the first X-ray source and the first X-ray detector of the X-ray device. Optionally, the method additionally comprises a second rotation of the first X-ray detector and the first X-ray source around the examination volume, as well as an acquisition of the third X-ray dataset via the first X-ray source and the first X-ray detector.

In particular, the first rotation involves a rotation through an angle corresponding to the angle between the first projection direction and the second projection direction. In particular, the second rotation involves a rotation through an angle corresponding to the angle between the second projection direction and the third projection direction. In particular, the first rotation and the second rotation have the same direction of rotation around the examination volume.

In particular, the first X-ray source and the second X-ray source are component parts of an X-ray device, for example a C-arm X-ray device or a computed tomography system. In particular, the X-ray device comprises no further X-ray source and no further X-ray detector.

The inventors have recognized that the method can be performed particularly cost-effectively through the use of just one X-ray source and one X-ray detector.

An embodiment of the invention may furthermore relates to a computer-implemented method for determining a four-dimensional image dataset, comprising a receiving of first X-ray datasets of an examination volume, wherein each X-ray dataset of the first X-ray datasets comprises a two-dimensional X-ray projection of the examination volume with respect to a projection direction, as well as, in addition, a receiving of second X-ray datasets of the examination volume, wherein each X-ray dataset of the second X-ray datasets comprises a two-dimensional X-ray projection of the examination volume with respect to a projection direction. The method further comprises a determining of a four-dimensional image dataset based on the first X-ray datasets and the second X-ray datasets. Optionally, the four-dimensional image dataset is provided, in which case the provision of the four-dimensional image dataset may comprise in particular a storing, a transmission and/or a displaying of the three-dimensional image dataset.

The receiving of the first X-ray datasets and the receiving of the second X-ray datasets may be accomplished in particular via an interface. The determining of the four-dimensional image dataset may be accomplished in particular via a computing unit. The optional provision of the four-dimensional image dataset may be accomplished in particular via the interface. The interface and the computing unit are in particular component parts of a determination system.

The inventors have recognized that by determining the four-dimensional image dataset based on the first and the second X-ray datasets it is possible to reduce or eliminate uncertainties due to vessel overlaps in individual X-ray projections. At the same time, the radiation dose with this method is the same or only minimally higher compared to the known standard methods of digital subtraction angiography.

According to a further aspect of an embodiment of the invention, the four-dimensional image dataset comprises a plurality of three-dimensional image datasets, each of the three-dimensional image datasets being based on a first X-ray dataset of the first X-ray datasets and a second X-ray dataset of the second X-ray datasets. In particular, a majority of the first X-ray datasets serves as a basis for at least two three-dimensional image datasets, and a majority of the second X-ray datasets serves as a basis for at least two three-dimensional image datasets. In particular, all except for one of the first X-ray datasets serve as a basis for at least two three-dimensional image datasets, and/or all except for one of the second X-ray datasets serve as a basis for at least two three-dimensional image datasets. In this case, a first X-ray dataset or a second X-ray dataset serves as a basis for a three-dimensional image dataset if the three-dimensional image dataset is based on the first X-ray dataset or on the second X-ray dataset, respectively.

The plurality of three-dimensional image datasets is in particular spatially three-dimensional, and the four-dimensional image dataset comprises in particular a temporal sequence of three-dimensional image datasets. In particular, therefore, a time coordinate is assigned to each of the three-dimensional image datasets.

The inventors have recognized that this aspect of an embodiment of the invention enables uncertainties in the three-dimensional image datasets due to vessel overlaps in individual X-ray projections to be reduced or eliminated. At the same time, however, the radiation dose accumulating in the examination volume is increased only slightly owing to the fact that a plurality of the first or second X-ray datasets serve as a basis for at least two three-dimensional image datasets.

According to a further aspect of an embodiment of the invention, the projection direction of the first X-ray dataset or its X-ray projection and the projection direction of the second X-ray dataset or its X-ray projection include an angle between 45° and 135°, in particular an angle between 60° and 120°, in particular an angle between 80° and 100°, in particular an angle between 85° and 95°.

The inventors have recognized that as a result of this choice of the angle between the first and the second projection direction close to orthogonality, an overlap of vessels with respect to the X-ray projection of the first X-ray dataset can be particularly well resolved by the X-ray projection of the second X-ray dataset, and vice versa.

According to a further aspect of an embodiment of the invention, the first X-ray dataset comprises a time point that corresponds to the time point of the acquisition of the X-ray projection of the first X-ray dataset, and the second X-ray dataset comprises a time point that corresponds to the time point of the acquisition of the X-ray projection of the second X-ray dataset, the time interval between the time point of the first X-ray dataset and the time point of the second X-ray dataset being less than 5 s, in particular less than 2 s, in particular less than 1 s, in particular less than 0.5 s, in particular less than 0.1 s, in particular less than 0.02 s.

If the time point of the first X-ray dataset and the time point of the second X-ray dataset are identical, the effects of scattered radiation during the acquisition or processing of the first X-ray projection and the second X-ray projection must be corrected through the acquisition of the other X-ray projection in each case.

The inventors have recognized that owing to the short time interval between the first and the second X-ray projection, only minor changes are produced in the examination volume, in particular in respect of the contrast agent concentration. Only minor artifacts are therefore produced in the first image dataset due to changes in the examination volume in the time between the acquisitions of the two X-ray projections.

According to a further possible aspect of an embodiment of the invention, each of the first X-ray datasets and each of the second X-ray datasets comprise a time point that corresponds to the time point of the acquisition of the associated X-ray projection. In this case the time points of the first X-ray datasets have a constant time interval, and the time points of the second X-ray datasets have the constant time interval.

If the time points of the first X-ray datasets are given by $t^{(1)}_i$, where $t^{(1)}_i < t^{(1)}_j$ for $i<j$, and if the time points of the second X-ray datasets are given by $t^{(2)}_i$, where $t^{(2)}_i < t^{(1)}_j$ for $i<j$, then $t^{(1)}_{i+1} - t^{(1)}_i = \Delta t$ applies for at least a plurality of the $t^{(1)}_i$, and $t^{(2)}_{i+1} - t^{(2)}_i = \Delta t$ applies for at least a plurality of the $t^{(2)}_i$.

If one of the three-dimensional image datasets is based on one of the first X-ray datasets having the assigned time point $t^{(1)}_i$, as well as on one of the second X-ray datasets having the assigned time point $t^{(2)}_j$, then the three-dimensional image dataset can be assigned a time coordinate t, where $\min(t^{(1)}_i, t^{(2)}_j) \leq t \leq \max(t^{(1)}_i, t^{(2)}_j)$. In particular, the time coordinate can form the midpoint of the interval $[\min(t^{(1)}_i, t^{(2)}_j); \max(t^{(1)}_i, t^{(2)}_j)]$.

If one of the three-dimensional image datasets is based on one of the first X-ray datasets having the assigned time point $t^{(1)}_i$, then it is based in particular either additionally on the X-ray dataset of the second X-ray datasets whose assigned time point is $\max(\{t^{(2)}_j \in \mathbb{T}^{(2)} | t^{(2)}_j \leq t^{(1)}_i\})$, or additionally on the X-ray dataset of the second X-ray datasets whose assigned time point is $\min(\{t^{(2)}_j \in \mathbb{T}^{(2)} | t^{(1)}_i \leq t^{(2)}_j\})$, where $\mathbb{T}^{(2)}$ denotes the set of all time points assigned to the second X-ray datasets. This applies in particular to a plurality of the three-dimensional image datasets, in particular to all of the three-dimensional image datasets.

The inventors have recognized that as a result of such a choice of the time points of the first X-ray datasets and the second X-ray datasets, a temporally uniform four-dimensional image dataset can be determined.

According to a further aspect of an embodiment of the invention, the time point of one of the second X-ray datasets corresponds to the midpoint in time between two time points of two temporally adjacent first X-ray datasets. In this case, two temporally adjacent first X-ray datasets have an assigned first time point and an assigned second time point, with the result that a time point between the first time point and the second time point is not assigned to any other of the second X-ray datasets.

Thus, if $t^{(1)}_i$ and $t^{(1)}_{i+1}$ denote the time points assigned to the temporally adjacent first X-ray datasets, where $t^{(1)}_i < t^{(1)}_{i+1}$, then the time point $t^{(2)}_j$ assigned to one of the second X-ray datasets is given by $t^{(2)}_j = (t^{(1)}_i + t^{(1)}_{i+1})/2$.

The inventors have recognized that as a result of such a choice of the time points of the first X-ray datasets and the second X-ray datasets, a temporally uniform four-dimensional image dataset can be determined.

According to a further possible aspect of an embodiment of the invention, the method additionally comprises a determining of a three-dimensional constraining image dataset of the examination volume, the plurality of the three-dimensional image datasets and/or the four-dimensional image dataset additionally being based on the three-dimensional constraining image dataset. The constraining image dataset can be determined in particular also by the receiving of the constraining image dataset. The constraining image dataset is determined in particular via the computing unit and/or the interface.

The inventors have recognized that by using a constraining image dataset it is possible to mask out structures in the examination volume outside of the vessels to be examined (for example bones, soft tissue structures, implants) from the first or second three-dimensional image dataset.

According to a further aspect of an embodiment of the invention, the determining of the constraining image dataset is based on the first X-ray datasets and on the second X-ray datasets. In particular, a three-dimensional reconstruction of the first X-ray datasets and the second X-ray datasets can be performed in this case (in particular also a reconstruction of only a portion of the first X-ray datasets and/or a portion of the second X-ray datasets), and the constraining image dataset can furthermore be based on a segmentation (e.g. a threshold value segmentation) of the reconstructed image dataset.

Alternatively, the constraining image dataset can also be determined by an application of a trained function to the first X-ray datasets and the second X-ray datasets. In particular, the input data of the trained function is based in this case on the first X-ray datasets and the second X-ray datasets, and the constraining image dataset is based on the output datasets of the trained function. A trained function may be in particular an artificial neural network, in particular a convolutional neural network.

The inventors have recognized that by this, it is possible to determine the four-dimensional image dataset in a self-consistent manner based on the first and the second X-ray datasets. In particular, the method is consequently not reliant on the constraining image dataset as input value.

According to a further possible aspect of an embodiment of the invention, the method additionally comprises a determining of first three-dimensional back-projection datasets based on the first X-ray datasets and on the constraining image dataset, and a determining of second three-dimensional back-projection datasets based on the second X-ray datasets and on the constraining image dataset. In this case, each of the three-dimensional image datasets is based on one of the first back-projection datasets and one of the second back-projection datasets. The first three-dimensional back-projection datasets and the second three-dimensional back-projection datasets can be determined in particular via the computing unit.

The inventors have recognized that an approximation of a three-dimensional reconstruction can be achieved particularly easily via a back-projection of a two-dimensional X-ray projection onto a three-dimensional constraining image dataset (resulting in a three-dimensional back-projection dataset). By using first back-projection datasets and second back-projection datasets it is simultaneously possible to take advantage of the fact that overlaps of vessels with respect to the first projections do not regularly occur in the second projections, and vice versa.

According to a further possible aspect of an embodiment of the invention, the determining of the four-dimensional image dataset comprises a multiplication of one of the first back-projection datasets with one of the second back-projection datasets. In particular, the determining of the plurality of three-dimensional image datasets comprises, for each of the three-dimensional image datasets, a multiplication of one of the first back-projection datasets with one of the second back-projection datasets. In particular, one of the three-dimensional image datasets is based on the result of the multiplication of one of the first back-projection datasets with one of the second back-projection datasets or is identical with the result. A multiplication is in particular a pixel-wise or voxel-wise multiplication.

The inventors have recognized that a particularly good approximation of a three-dimensional reconstruction of the examination volume can be achieved based on the multiplication of two back-projection datasets.

According to a further possible aspect of an embodiment of the invention, the method additionally comprises an acquisition of the first X-ray datasets via a first X-ray source and a first X-ray detector of an X-ray device, as well as an acquisition of the second X-ray datasets via a second X-ray source and a second X-ray detector of the X-ray device. The first X-ray source and the second X-ray source may in particular be different X-ray sources of a multisource X-ray device. The first X-ray detector and the second X-ray detector may in particular be different X-ray detectors of the multisource X-ray device.

The inventors have recognized that by using a first and a second X-ray source or, as the case may be, a first and a second X-ray detector it is possible to choose a particularly small time interval between the acquisition of an X-ray dataset of the first X-ray datasets and an X-ray dataset of the second X-ray datasets, since the first X-ray source and the first X-ray detector or, as the case may be, the second X-ray source and the second X-ray detector can be arranged such that the angle between the optical axes virtually corresponds to the angle between the respective projection directions. As a result, the time interval is no longer substantially determined by the mechanical movability of X-ray source and X-ray detector, but by the electronic control of X-ray sources and X-ray detectors or, as the case may be, by the physical properties of the respective sources of scattered radiation.

According to a further possible aspect of an embodiment of the invention, the method additionally comprises an acquisition of one of the first X-ray datasets via a first X-ray source and a first X-ray detector of a X-ray device, a first rotation of the first X-ray detector and the first X-ray source around the examination volume, an acquisition of one of the second X-ray datasets via the first X-ray source and the first X-ray detector of the X-ray device, as well as an optional second rotation of the first X-ray detector and the first X-ray source around the examination volume.

In particular, the first rotation involves a rotation through an angle corresponding to the angle between the projection direction of one X-ray dataset of the first X-ray datasets and the projection direction of one X-ray dataset of the second X-ray datasets. In particular, the second rotation involves a rotation through an angle corresponding to the angle between the projection direction of one X-ray dataset of the second X-ray datasets and the projection direction of another X-ray dataset of the first X-ray datasets. In particular, the first rotation and the second rotation have the same direction of rotation around the examination volume. In particular, the angles of the first rotation and the angles of the second rotation are the same.

The first X-ray source and the second X-ray source are in particular component parts of an X-ray device, for example a C-arm X-ray device or a computed tomography system. In particular, the X-ray device comprises no further X-ray source and no further X-ray detector.

The inventors have recognized that the method can be performed particularly cost-effectively through the use of just one X-ray source and one X-ray detector.

An embodiment of the invention also relates to a determination system for determining an image dataset of an examination volume, comprising an interface embodied for receiving a first X-ray dataset of the examination volume, wherein the first X-ray dataset comprises a two-dimensional first X-ray projection of the examination volume with respect to a first projection direction, further embodied for receiving a second X-ray dataset of the examination volume, wherein the second X-ray dataset comprises a two-dimensional second X-ray projection of the examination volume with respect to a second projection direction; and a computing unit embodied for determining a first three-dimensional image dataset of the examination volume based on the first X-ray projection and the second X-ray projection.

An embodiment of the invention may also relate to a determination system for determining an image dataset of an examination volume, comprising an interface embodied for receiving a first X-ray dataset of the examination volume, wherein the first X-ray dataset comprises a two-dimensional first X-ray projection of the examination volume with respect to a first projection direction, further embodied for receiving a second X-ray dataset of the examination volume, wherein the second X-ray dataset comprises a two-dimensional second X-ray projection of the examination volume with respect to a second projection direction, further embodied for receiving a third X-ray dataset of the examination volume, wherein the third X-ray dataset comprises a two-dimensional third X-ray projection of the examination volume with respect to a third projection direction; and a computing unit embodied for determining a first three-dimensional image dataset of the examination volume based on the first X-ray projection and the second X-ray projection, further embodied for determining a second three-dimensional image dataset of the examination volume based on the second X-ray projection and the third X-ray projection.

The invention may also relate to a determination system for determining a four-dimensional image dataset of an examination volume, comprising:

an interface embodied for receiving first X-ray datasets of the examination volume, wherein each X-ray dataset of the first X-ray datasets comprises a two-dimensional X-ray projection of the examination volume with respect to a projection direction, further embodied for receiving second X-ray datasets of the examination volume, wherein each X-ray dataset of the second X-ray datasets comprises a two-dimensional X-ray projection of the examination volume with respect to a projection direction; and a computing unit embodied for determining a four-dimensional image dataset based on the first X-ray datasets and the second X-ray datasets.

These determination systems may be embodied in particular for performing the above-described embodiments of inventive methods and their aspects. A determination system is embodied to perform these methods and their aspects, while the interface and/or the computing unit are embodied to perform the corresponding method steps.

An embodiment of the invention also relates to an X-ray device comprising one of the described determination systems. The X-ray device may in particular comprise a first X-ray source and a first X-ray detector. In addition, the X-ray device may in particular also comprise a second X-ray source and a second X-ray detector. The X-ray device may in particular be a C-arm X-ray device, a computed tomography system or a multisource X-ray device.

An embodiment of the invention also relates to computer program products comprising a computer program and a computer-readable medium. A largely software-based implementation has the advantage that determination systems already in use can also be easily upgraded by way of a software update in order to operate in the manner according to embodiments of the invention. As well as the computer program, such a computer program product may where applicable comprise additional constituent parts such as e.g. a set of documentation and/or additional components, including hardware components, such as e.g. hardware keys (dongles, etc.) to enable use of the software.

The X-ray datasets of the first plurality of X-ray datasets may also be referred to as first X-ray datasets, while the X-ray datasets of the second plurality of X-ray datasets may also be referred to as second X-ray datasets. The X-ray projections of the first plurality of X-ray datasets may also be referred to as first X-ray projections, while the X-ray projections of the second plurality of X-ray datasets may also be referred to as second X-ray projections. The time points of the first plurality of X-ray datasets may also be referred to as first time points, while the time points of the second plurality of X-ray datasets may also be referred to as second time points. The projection directions of the first X-ray projections may also be referred to as first projection directions, while the projection directions of the second X-ray projections may also be referred to as second projection directions.

Further possible aspects or example embodiments of the invention are listed below.

Aspect A.1: An embodiment is directed to a computer-implemented method for determining a three-dimensional image dataset of the examination volume, comprising:
  receiving a first X-ray dataset of an examination volume, wherein the first X-ray dataset comprises a two-dimensional first X-ray projection of the examination volume with respect to a first projection direction,
  receiving a second X-ray dataset of the examination volume, wherein the second X-ray dataset comprises a two-dimensional second X-ray projection of the examination volume with respect to a second projection direction,
  determining a first three-dimensional image dataset of the examination volume based on the first X-ray projection and the second X-ray projection.

Aspect A.2: The method according to aspect A.1, wherein the first projection direction and the second projection direction include an angle between 45° and 135°, in particular an angle between 60° and 120°, in particular an angle between 80° and 100°, in particular an angle between 85° and 95°.

Aspect A.3: The method according to aspect A.1 or A.2, wherein the first X-ray dataset comprises a first time point, the first time point corresponding to the time point of the acquisition of the first X-ray projection,
  wherein the second X-ray dataset comprises a second time point, the second time point corresponding to the time point of the acquisition of the second X-ray projection, and wherein the time interval between the first time point and the second time point is less than 5 s, in particular less than 2 s, in particular less than 1 s, in particular less than 0.5 s, in particular less than 0.1 s, in particular less than 0.02 s.

Aspect A.4: The method according to one of aspects A.1 to A.3, further comprising:
  determining a three-dimensional constraining image dataset of the examination volume,
wherein the determining of the first three-dimensional image dataset is additionally based on the constraining image dataset.

Aspect A.5: The method according to aspect A.4, wherein the determining of the constraining image dataset is based on the first X-ray dataset and the second X-ray dataset.

Aspect A.6: The method according to aspect A.4 or A.5, further comprising:
  determining a first three-dimensional back-projection dataset based on the first X-ray dataset and on the constraining image dataset,
  determining a second three-dimensional back-projection dataset based on the second X-ray dataset and on the constraining image dataset,
wherein the first three-dimensional image dataset is based on the first three-dimensional back-projection dataset and on the second three-dimensional back-projection dataset.

Aspect A.7: The method according to A.6, wherein the determining of the first three-dimensional image dataset comprises a multiplication of the first back-projection dataset with the second back-projection dataset.

Aspect A.8: The method according to one of aspects A.1 to A.7, further comprising:
  acquiring the first X-ray dataset via a first X-ray source and a first X-ray detector of an X-ray device,
  acquiring the second X-ray dataset via a second X-ray source and a second X-ray detector of the X-ray device.

Aspect A.9: The method according to one of aspects A.1 to A.7, further comprising:
  acquiring the first X-ray dataset via a first X-ray source and a first X-ray detector of an X-ray device,
  a first rotation of the first X-ray detector and the first X-ray source around the examination volume,
  acquiring the second X-ray dataset via the first X-ray source and the first X-ray detector of the X-ray device.

Aspect A.10: A determination system for determining an image dataset of an examination volume, comprising
  an interface embodied for receiving a first X-ray dataset of the examination volume, wherein the first X-ray dataset comprises a two-dimensional first X-ray projection of the examination volume with respect to a first projection direction,
  further embodied for receiving a second X-ray dataset of the examination volume, wherein the second X-ray dataset comprises a two-dimensional second X-ray projection of the examination volume with respect to a second projection direction,
  a computing unit embodied for determining a first three-dimensional image dataset of the examination volume based on the first X-ray projection and the second X-ray projection.

Aspect A.11: An X-ray device comprising a determination system according to aspect A.10.

Aspect A.12: A computer program product comprising a computer program which can be loaded directly into a memory of a determination system, in particular a determination system according to A.10, having program sections for performing all steps of the method according to one of the embodiments or aspects A.1 to A.9 when the program sections are executed by the determination system.

Aspect A.13: A computer-readable storage medium on which program sections that can be read and executed by a determination system (in particular a determination system according to A.10) are stored in order to perform all steps of the method according to one of the embodiments or one of aspects A.1 to A.9 when the program sections are executed by the determination system.

Aspect B.1: A computer-implemented method for determining a three-dimensional image dataset of an examination volume, comprising:
receiving a first X-ray dataset of the examination volume, wherein the first X-ray dataset comprises a two-dimensional first X-ray projection of the examination volume with respect to a first projection direction,
receiving a second X-ray dataset of the examination volume,
wherein the second X-ray dataset comprises a two-dimensional second X-ray projection of the examination volume with respect to a second projection direction,
receiving a third X-ray dataset of the examination volume, wherein the third X-ray dataset comprises a two-dimensional third X-ray projection of the examination volume with respect to a third projection direction,
determining a first three-dimensional image dataset of the examination volume based on the first X-ray projection, the second X-ray projection and the third X-ray projection.

Aspect B.2: The method according to aspect B.1, wherein the first projection direction and the second projection direction include an angle between 45° and 135°, in particular an angle between 60° and 120°, in particular an angle between 80° and 100°, in particular an angle between 85° and 95°, and/or wherein the second projection direction and the third projection direction include an angle between 45° and 135°, in particular an angle between 60° and 120°, in particular an angle between 80° and 100°, in particular an angle between 85° and 95°.

Aspect B.3: The method according to aspect B.1 or B.2, wherein the first X-ray dataset comprises a first time point, the first time point corresponding to the time point of the acquisition of the first X-ray projection,
wherein the second X-ray dataset comprises a second time point, the second time point corresponding to the time point of the acquisition of the second X-ray projection, wherein the third X-ray dataset comprises a third time point, the third time point corresponding to the time point of the acquisition of the third X-ray projection,
and wherein the time interval between the first time point and the second time point is less than 5 s, in particular less than 2 s, in particular less than 1 s, in particular less than 0.5 s, in particular less than 0.1 s, in particular less than 0.02 s, and/or wherein the time interval between the second time point and the third time point is less than 5 s, in particular less than 2 s, in particular less than 1 s, in particular less than 0.5 s, in particular less than 0.1 s, in particular less than 0.02 s.

Aspect B.4: The method according to aspect B.3, wherein the second time point corresponds to the midpoint in time between the first time point and of the third time point.

Aspect B.5: The method according to one of aspects B.1 to B.4, wherein the first projection direction and the third projection direction include an angle of less than 45°, in particular an angle of less than 30°, in particular an angle of less than 10°, in particular an angle of less than 5°.

Aspect B.6: The method according to one of aspects B.1 to B.5, further comprising:
determining a three-dimensional constraining image dataset of the examination volume,
wherein the determining of the first three-dimensional image dataset is additionally based on the constraining image dataset,
and wherein the determining of the second three-dimensional image dataset is additionally based on the constraining image dataset.

Aspect B.7: The method according to aspect B.6, wherein the determining of the constraining image dataset is based on the first X-ray dataset, the second X-ray dataset and/or the third X-ray dataset.

Aspect B.8: The method according to aspect B.6 or B.7, further comprising:
determining a first three-dimensional back-projection dataset based on the first X-ray dataset and on the constraining image dataset,
determining a second three-dimensional back-projection dataset based on the second X-ray dataset and on the constraining image dataset,
determining a third three-dimensional back-projection dataset based on the third X-ray dataset and on the constraining image dataset,
wherein the first three-dimensional image dataset is based on the first three-dimensional back-projection dataset and on the second three-dimensional back-projection dataset, and wherein the second three-dimensional image dataset is based on the second three-dimensional back-projection dataset and on the third three-dimensional back-projection dataset.

Aspect B.9: The method according to aspect B.8, wherein the determining of the first three-dimensional image dataset comprises a multiplication of the first back-projection dataset with the second back-projection dataset, and wherein the determining of the second three-dimensional image dataset comprises a multiplication of the second back-projection dataset with the third back-projection dataset.

Aspect B.10: The method according to one of the preceding aspects B.1 to B.9, further comprising:
acquiring the first X-ray dataset via a first X-ray source and a first X-ray detector of an X-ray device,
acquiring the second X-ray dataset via a second X-ray source and a second X-ray detector of the X-ray device.
acquiring the third X-ray dataset via the first X-ray source and the first X-ray detector of the X-ray device.

Aspect B.11: The method according to one of aspects B.1 to B.9, further comprising:
acquiring the first X-ray dataset via a first X-ray source and a first X-ray detector of an X-ray device,
a first rotation of the first X-ray detector and the first X-ray source around the examination volume,
acquiring the second X-ray dataset via the first X-ray source and the first X-ray detector of the X-ray device,
a second rotation of the first X-ray detector and the first X-ray source around the examination volume,
acquiring the third X-ray dataset via the first X-ray source and the first X-ray detector of the X-ray device.

Aspect B.12. A determination system for determining an image dataset of an examination volume, comprising
an interface embodied for receiving a first X-ray dataset of the examination volume, wherein the first X-ray dataset comprises a two-dimensional first X-ray projection of the examination volume with respect to a first projection direction, further embodied for receiving a second X-ray dataset of the examination volume, wherein the second X-ray dataset comprises a two-dimensional second X-ray projection of the examination volume with respect to a second projection direction, further embodied for receiving a third X-ray dataset of the examination volume, wherein the third X-ray dataset comprises a two-dimensional third X-ray projection of the examination volume with respect to a third projection direction, a computing unit embodied for determining a first three-dimensional image dataset of the examination volume based on the first X-ray projection and the second X-ray projection, further embodied for determining a second three-dimensional image dataset of the examination volume based on the second X-ray projection and the third X-ray projection.

Aspect B.13: An X-ray device comprising a determination system according to B.12.

Aspect B.14: A computer program product comprising a computer program which can be loaded directly into a memory of a determination system, in particular a determination system according to B.12, having program sections for performing all steps of the method according to one of the embodiments or aspects B.1 to B.11 when the program sections are executed by the determination system.

Aspect B.15: A computer-readable storage medium on which program sections that can be read and executed by a determination system (in particular a determination system according to B.12) are stored in order to perform all steps of the method according to one of the embodiments or aspects B.1 to B.11 when the program sections are executed by the determination system.

Aspect C.1: A computer-implemented method for determining a four-dimensional image dataset, comprising:

receiving first X-ray datasets of an examination volume, wherein each X-ray dataset of the first X-ray datasets comprises a two-dimensional X-ray projection of the examination volume with respect to a projection direction, receiving second X-ray datasets of the examination volume, wherein each X-ray dataset of the second X-ray datasets comprises a two-dimensional X-ray projection of the examination volume with respect to a projection direction, determining a four-dimensional image dataset based on the first X-ray datasets and the second X-ray datasets.

Aspect C.2: The method according to aspect C.1, wherein the four-dimensional image dataset comprises a plurality of three-dimensional image datasets, wherein each of the three-dimensional image datasets is based on a first X-ray dataset of the first X-ray datasets and on a second X-ray dataset of the second X-ray datasets.

Aspect C.3: The method according to aspect C.2, wherein the projection direction of the first X-ray dataset and the projection direction of the second X-ray dataset include an angle between 45° and 135°, in particular an angle between 60° and 120°, in particular an angle between 80° and 100°, in particular an angle between 85° and 95°.

Aspect C.4: The method according to aspect C.2 or C.3, wherein the first X-ray dataset comprises a time point that corresponds to the time point of the acquisition of the X-ray projection of the first X-ray dataset, wherein the second X-ray dataset comprises a time point that corresponds to the time point of the acquisition of the X-ray projection of the second X-ray dataset, and wherein the time interval between the time point of the first X-ray dataset and the time point of the second X-ray dataset is less than 5 s, in particular less than 2 s, in particular less than 1 s, in particular less than 0.5 s, in particular less than 0.1 s, in particular less than 0.02 s.

Aspect C.5: The method according to one of aspects C.1 to C.4, wherein each of the first X-ray datasets and each of the second X-ray datasets comprises a time point that corresponds to the time point of the acquisition of the associated X-ray projection, wherein the time points of the first X-ray datasets have a constant time interval, wherein the time points of the second X-ray datasets have the constant time interval.

Aspect C.6: The method according to aspect C.5, wherein the time point of one of the second X-ray datasets corresponds to the midpoint in time between two time points of two temporally adjacent first X-ray datasets.

Aspect C.7: The method according to one of aspects C.2 to C.6, further comprising:

determining a three-dimensional constraining image dataset of the examination volume, wherein the plurality of three-dimensional image datasets and/or the four-dimensional image dataset are additionally based on the three-dimensional constraining image dataset.

Aspect C.8: The method according to aspect C.7, wherein the determining of the constraining image dataset is based on the first X-ray datasets and on the second X-ray datasets, in particular on the application of a trained function to the first X-ray datasets and the second X-ray datasets.

Aspect C.9: The method according to aspect C.7 or C.8, further comprising:

determining first three-dimensional back-projection datasets based on the first X-ray datasets and on the constraining image dataset, determining second three-dimensional back-projection datasets based on the second X-ray datasets and on the constraining image dataset, wherein each of the three-dimensional image datasets is based on one of the first back-projection datasets and one of the second back-projection datasets.

Aspect C.10: The method according to aspect C.9, wherein the determining of the four-dimensional image dataset comprises a multiplication of one of the first back-projection datasets with one of the second back-projection datasets.

Aspect C.11: The method according to one of aspects C.1 to C.10, further comprising:

acquiring the first X-ray datasets via a first X-ray source and a first X-ray detector of an X-ray device, acquiring the second X-ray datasets via a second X-ray source and a second X-ray detector of the X-ray device.

Aspect C.12: The method according to one of aspects C.1 to C.10, further comprising:

acquiring one of the first X-ray datasets via a first X-ray source and a first X-ray detector of an X-ray device, a first rotation of the first X-ray detector and the first X-ray source around the examination volume, acquiring one of the second X-ray datasets via the first X-ray source and the first X-ray detector of the X-ray device, a second rotation of the first X-ray detector and the first X-ray source around the examination volume.

Aspect C.13: A determination system for determining a four-dimensional image dataset, comprising:

an interface embodied for receiving first X-ray datasets of an examination volume, wherein each X-ray dataset of the first X-ray datasets comprises a two-dimensional X-ray projection of the examination volume with respect to a projection direction, further embodied for receiving second X-ray datasets of the examination volume, wherein each X-ray dataset of the second X-ray datasets comprises a two-dimensional X-ray projection of the examination volume with respect to a projection direction, a computing unit embodied for determining a four-dimensional image dataset based on the first X-ray datasets and the second X-ray datasets.

Aspect C.14: An X-ray device comprising a determination system according to aspect C.13.

Aspect C.15: A computer program product comprising a computer program which can be loaded directly into a memory of a determination system, in particular a determination system according to C.13, having program sections for performing all steps of the method according to one of aspects C.1 to C.12 when the program sections are executed by the determination system.

Aspect C.16: A computer-readable storage medium on which program sections that can be read and executed by a determination system (in particular a determination system according to C.13) are stored in order to perform all steps of the method according to one of aspects C.1 to C.12 when the program sections are executed by the determination system.

FIG. 1 shows an examination volume VOL containing two vessels VES.1, VES.2, as well as a first three-dimensional image dataset ID.1. In this case the field of view of the first three-dimensional image dataset ID.2 corresponds to the examination volume. In the example embodiment shown, the examination volume VOL comprises a first vessel VES.1 and a second vessel VES.2, the first vessel VES.1 branching into two branches within the examination volume VOL. It is also possible for the examination volume VOL to comprise no vessel VES.1, VES.2, precisely one vessel VES.1, VES.2, or more than two vessels VES.1, VES.2. In addition to the vessels VES.1, VES.2, the examination volume VOL comprises further structures OS.1, OS.2, which in particular are not imaged in the first three-dimensional image dataset ID.1 if the first three-dimensional image dataset ID.1 is a difference image dataset.

In the example embodiment shown, the examination volume VOL and the first three-dimensional image dataset ID.1 are extended with respect to a first direction x, a second direction y and a third direction z. The first direction x, the second direction y and the third direction z are pairwise orthogonal in this case.

Figure 2:
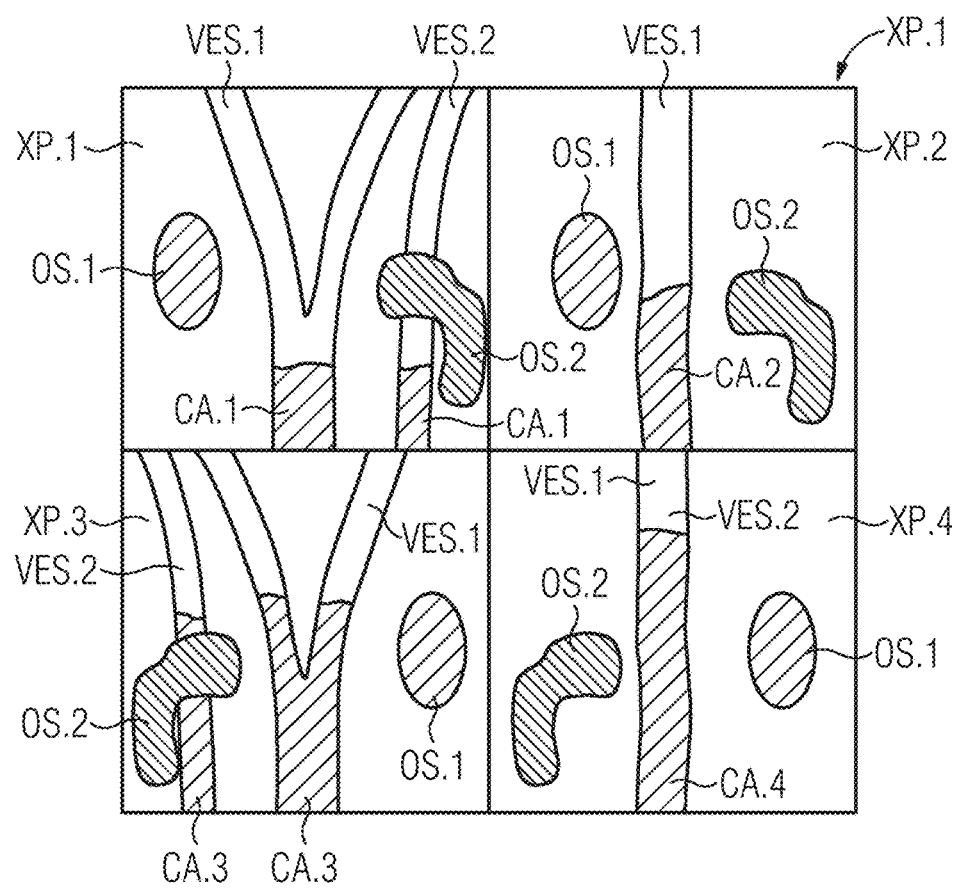
FIG. 2 shows X-ray projections of the examination volume.

FIG. 2 shows X-ray projections XP.1, . . . , XP.4 of the examination volume VOL in respect of a second X-ray energy. In the example embodiment shown, four two-dimensional X-ray projections XP.1, . . . , XP.4 are depicted, though the inventive methods may also be used in the context of more or fewer two-dimensional X-ray projections XP.1, . . . , XP.4.

Each of the two-dimensional X-ray projections XP.1, . . . , XP.4 is in this case an X-ray projection of the examination volume VOL with respect to a projection direction. The X-ray projection XP.1 is in this case an X-ray projection of the examination volume VOL with respect to a projection direction, the projection direction being antiparallel to the first direction x. The X-ray projection XP.2 is an X-ray projection of the examination volume VOL with respect to a projection direction, the projection direction being antiparallel to the second direction y. The X-ray projection XP.3 is an X-ray projection of the examination volume VOL with respect to a projection direction, the projection direction being parallel to the first direction x. The X-ray projection XP.4 is an X-ray projection of the examination volume VOL with respect to a projection direction, the projection direction being parallel to the second direction y.

In the example embodiment shown, each of the two-dimensional X-ray projections XP.1, . . . , XP.4 images the vessels VES.1, VES.2 contained in the examination volume VOL. Other structures OS.1, OS.2 in the examination volume VOL are also imaged by the two-dimensional X-ray projections XP.1, . . . , XP.4.

At the different time points of the acquisition of the two-dimensional X-ray projections XP.1, . . . , XP.4, the vessels VES.1, VES.2 comprise concentrations CA.1, . . . , CA.4 of contrast agent that vary with time. In this case, the vessels VES.1, VES.2 have a contrast agent concentration CA.1 during the acquisition of the X-ray projection XP.1. Furthermore, the vessels VES.1, VES.2 have a contrast agent concentration CA.2 during the acquisition of the X-ray projection XP.2. The vessels VES.1, VES.2 furthermore have a contrast agent concentration CA.3 during the acquisition of the X-ray projection XP.3. In addition, the vessels VES.1, VES.2 have a contrast agent concentration CA.4 during the acquisition of the X-ray projection XP.4. The contrast agent is in this case an X-ray contrast agent, so that the respective contrast agent concentration CA.1, . . . , CA.4 of the contrast agent can be determined from the X-ray projections XP.1, . . . , XP.4. The contrast agent concentration CA.1, . . . , CA.4 varies with time as a result of a static or dynamic flow of fluid in the vessels VES.1, VES.2. In the example embodiment shown, the fluid is blood.

Figure 3:
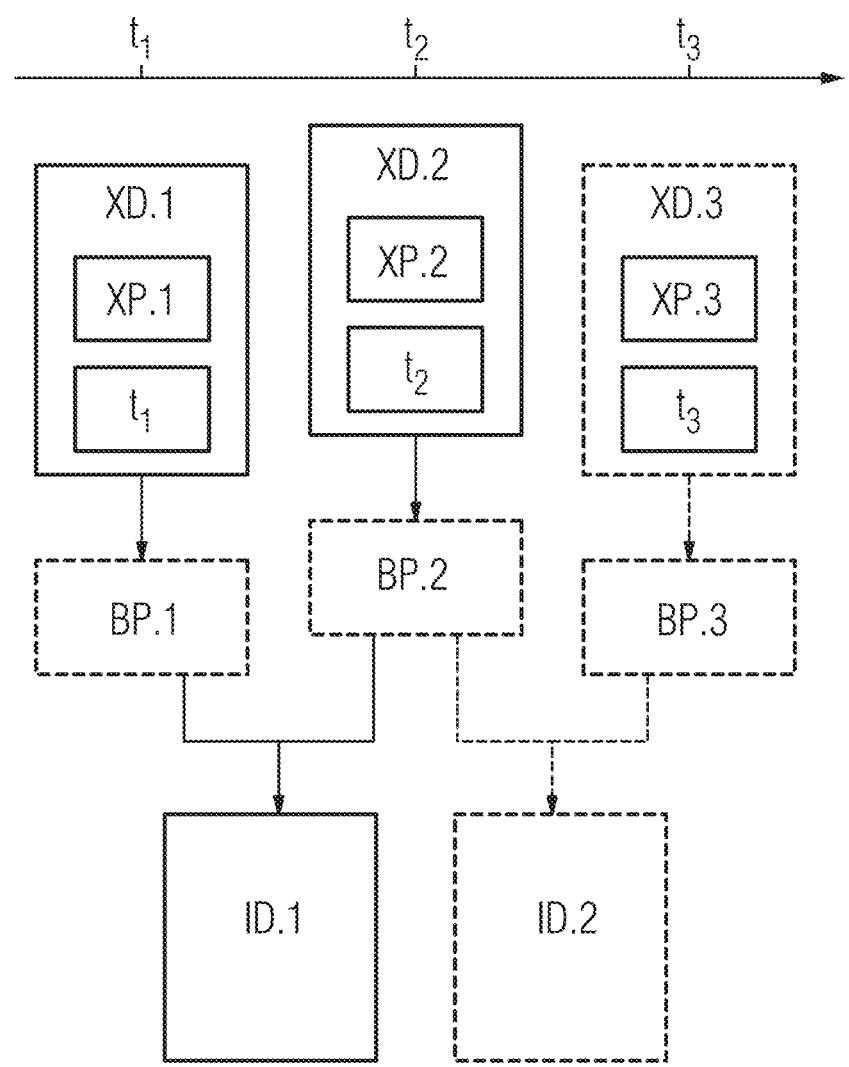
FIG. 3 shows a first, a second and a third X-ray dataset.

FIG. 3 shows a first X-ray dataset XD.1, a second X-ray dataset XD.2 and a third X-ray dataset XD.3. Herein, the first X-ray dataset XD.1 comprises a first X-ray projection XP.1 of an examination volume VOL with respect to a first projection direction v1, as well as a first time point t1, the first time point t1 corresponding to the time point of the acquisition of the first X-ray projection XP.1. Also, the second X-ray dataset XD.2 comprises a second X-ray projection XP.2 of the examination volume VOL with respect to a second projection direction v2, as well as a second time point t2, the second time point t2 corresponding to the time point of the acquisition of the second X-ray projection XP.2. The third X-ray dataset XD.3 furthermore comprises a third X-ray projection XP.3 of the examination volume VOL with respect to a third projection direction v3, as well as a third time point t3, the third time point t3 corresponding to the time point of the acquisition of the third X-ray projection XP.3.

In the example embodiment shown, the first time point $t_1$, the second time point $t_2$ and the third time point $t_3$ are pairwise distinct. Furthermore, the second time point $t_2$ is located between the first time point $t_1$ and the third time point $t_3$ in time. In particular, it holds for the second time point that $t_2=t_1+a \cdot (t_3-t_1)$, where $0 \leq a \leq 1$. In particular, the parameter a may be chosen such that a=0.5, in which case the second time point $t_2$ is the midpoint in time between the first time point $t_1$ and the third time point $t_3$. The time interval between the first time point $t_1$ and the second time point $t_2$ may also be designated by $\Delta t_1 = t_2 - t_1$, and the time interval between the second time point $t_2$ and the third time point $t_3$ may also be designated by $\Delta t_2 = t_3 - t_2$; in this notation the parameter a is yielded as $a = \Delta t_1 / (\Delta t_1 + \Delta t_2)$.

In this example embodiment, the time interval $\Delta t_1$ between the first time point $t_1$ and the second time point $t_2$ is less than 5 s, in particular less than 2 s, in particular less than 1 s, in particular less than 0.5 s. In particular, it also holds that $\Delta t_1 = \Delta t_2 = \Delta t$.

The X-ray datasets XD.1, . . . , XD.3 may also comprise further data, for example the X-ray voltage used for the X-ray projection XP.1, . . . , XP.3, or the X-ray current, or other relevant parameters for the X-ray projection. The X-ray datasets XD.1, . . . , XD.3 may also comprise in particular the projection direction $v_1, v_2, v_3$ of the associated X-ray projection XP.1, . . . , XP.3.

Figure 4:
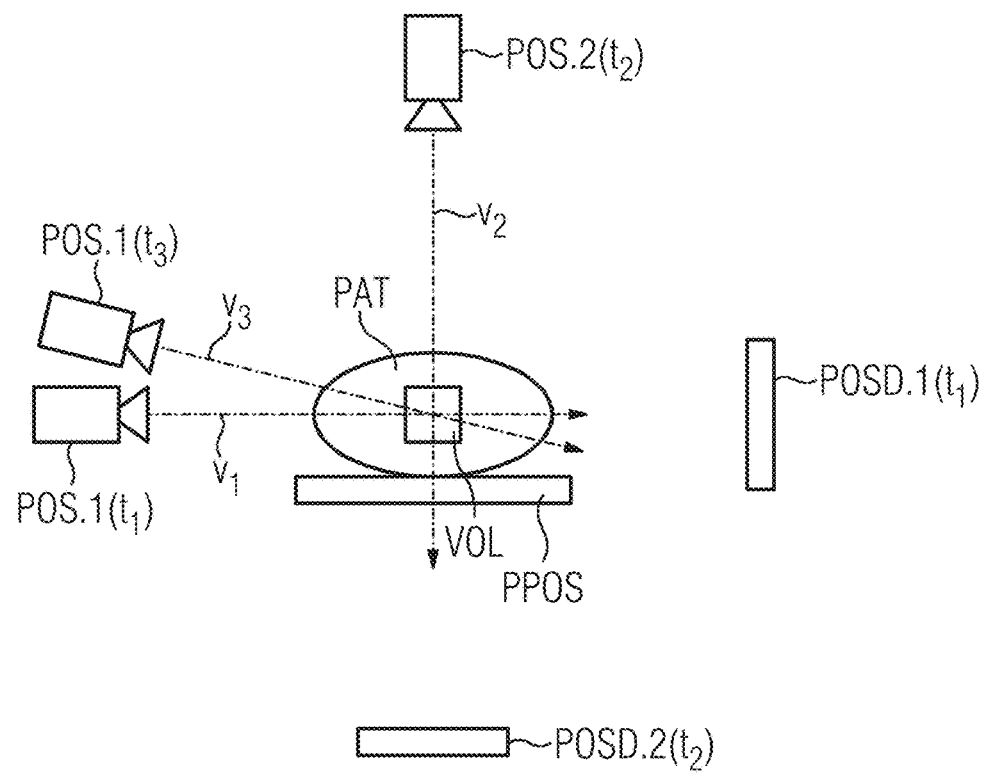
FIG. 4 shows a first example embodiment of a geometric arrangement of an acquisition of a first, a second and a third X-ray projection.

FIG. 4 shows a first example embodiment of a geometric arrangement of an acquisition of a first X-ray projection XP.1, a second X-ray projection XP.2 and a third X-ray projection XP.3.

The examination volume VOL is in this case part of a patient PAT that is positioned on a patient support and positioning device PPOS. The X-ray projections XP.1, ..., XP.3 are determined in this case via a first X-ray source SRC.1 and a first X-ray detector DTC.1, as well as via a second X-ray source SRC.2 and a second X-ray detector DTC.2. The X-ray sources SRC.1, SRC.2 and the X-ray detectors DTC.1, DTC.2 are in this case in particular part of an X-ray device XSYS.

In this example embodiment, the first X-ray dataset XD.1 and the third X-ray dataset XD.3 are acquired via the first X-ray source SRC.1 and the first X-ray detector, and the second X-ray dataset XD.2 is acquired via the second X-ray source SRC.2 and the second X-ray detector. The parameter t1 denotes the time point of the acquisition of the first X-ray projection XP.1, t2 the time point of the acquisition of the second X-ray projection XP.2, and t3 the time point of the acquisition of the third X-ray position.

Also shown are the position POS.1($t_1$) of the first X-ray source SRC.1 at the time point $t_1$, the position SRC.1($t_3$) of the first X-ray source at the time point $t_3$, the position POS.2($t_2$) of the second X-ray source SRC.2 at the time point $t_2$, the position POSD.1($t_1$) of the first X-ray detector DTC.1 at the time point $t_1$, and the position POSD.2($t_2$) of the second X-ray detector DTC.2 at the time point $t_2$. The remaining positions at the remaining time points have not been included in the drawing since the position of an X-ray detector DTC.1, DTC.2 is generally located on the side of the examination volume VOL disposed opposite the X-ray source SRC.1, SRC.2.

The first projection direction $v_1$ of the first X-ray projection, the second projection direction $v_2$ of the second X-ray projection and the third projection direction $v_3$ of the third X-ray projection are also shown. The angle $\varphi(v_1, v_2)$ which the first projection direction $v_1$ and the second projection direction $v_2$ include is calculated in this case as $\varphi(v_1, v_2)=\arccos(v_1 \circ v_2/|v_1\|v_2|)$, where $v_1 \circ v_2$ is the scalar product of $v_1$ and $v_2$, and where $|v_1|$ is the length of $v_1$.

In this example embodiment, the first projection direction $v_1$ and the second projection direction $v_2$ include an angle $\varphi(v_1, v_2)$ between 45° and 135°, in particular an angle between 60° and 120°, in particular an angle between 80° and 100°, in particular an angle between 85° and 95°. Furthermore, the second projection direction $v_2$ and the third projection direction $v_3$ include an angle $\varphi(v_2, v_3)$ between 45° and 135°, in particular an angle between 60° and 120°, in particular an angle between 80° and 100°, in particular an angle between 85° and 95°.

The angle between the respective projection directions $v_1$, $v_2$, $v_3$ is achieved in this example embodiment in that both the first X-ray source SRC.1, simultaneously with the first X-ray detector DTC.1, and the second X-ray source SRC.2, simultaneously with the second X-ray detector DTC.2, rotate around the examination volume VOL, in particular at a constant angular velocity ω and on a circular trajectory in each case. This yields the angles $\varphi(v_1, v_2)=\varphi_0+\omega \cdot \Delta t_1$ and $\varphi(v_2, v_3)=\varphi_0+\omega \cdot \Delta t_2$, where $\varphi_0$ is the constant angle between the direction vector from the first X-ray source SRC.1 to the first X-ray detector DTC.1 and the direction vector from the second X-ray source SRC.2 to the second X-ray detector DTC.2. Advantageously, the angle chosen is $\varphi_0=90°$.

Figure 5:
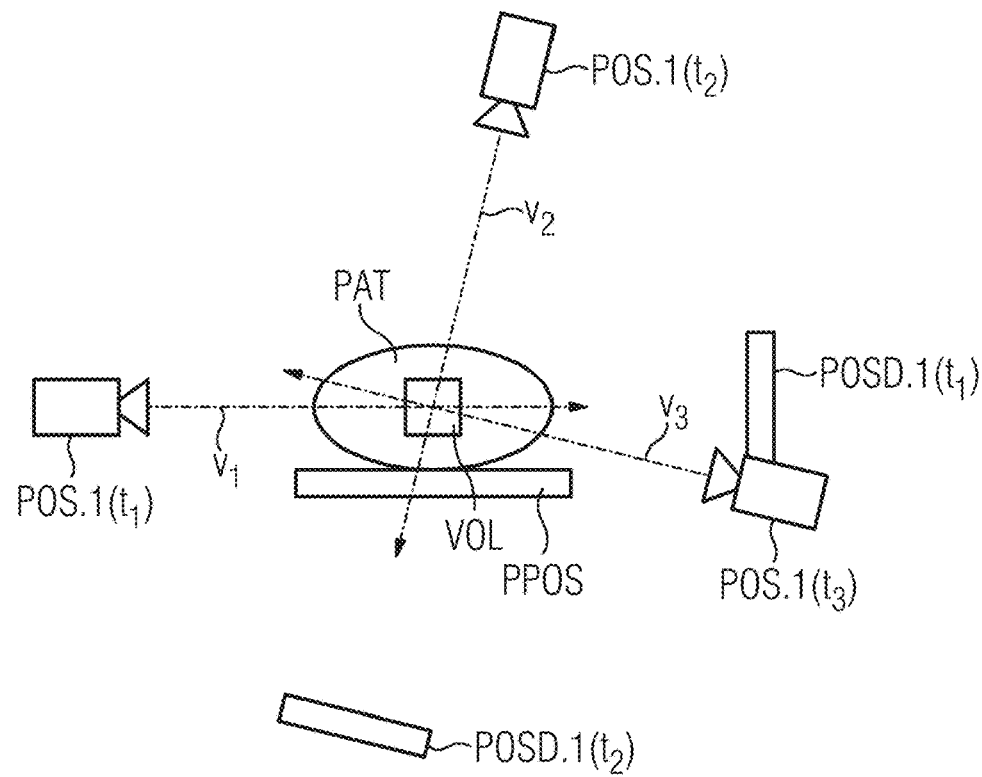
FIG. 5 shows a second example embodiment of a geometric arrangement of an acquisition of a first, a second and a third X-ray projection.

FIG. 5 shows a second example embodiment of a geometric arrangement of an acquisition of a first X-ray projection XP.1, a second X-ray projection XP.2 and a third X-ray projection XP.3. The X-ray projections XP.1, ..., XP.3 are acquired in this case via a first X-ray source SRC.1 and a first X-ray detector DTC.1.

The positions POS.1($t_1$), POS.1($t_2$), POS.1($t_3$) of the first X-ray source SRC.1 at the time points $t_1$, $t_2$, $t_3$ of the acquisition of the X-ray projections XP.1, XP.2, XP.3 are shown. For clarity of illustration reasons, the positions of the first X-ray detector DTC.1 have not been depicted, the latter being located on the side of the examination volume VOL opposite the first X-ray source SRC.1 in each case, and orthogonally to the respective projection direction $v_1, v_2, v_3$.

With the acquisition geometry shown in FIG. 5, in particular the same X-ray projections XP.1, XP.2, XP.3 can be acquired at the same time points $t_1$, $t_2$, $t_3$ as with the acquisition geometry shown in FIG. 4. In this case, although there is in fact a change with respect to the third projection direction $v_3$ in the direction in which the X-ray radiation passes through the examination volume VOL, this has, in a good approximation, no effects on the third X-ray projection XP.3 (in particular if effects of the scattered radiation are not taken into account).

In the example embodiment shown, the first X-ray source SRC.1 and the first X-ray detector DTC.1 rotate simultaneously at an angular velocity ω on a circular trajectory around the examination volume. Alternatively, the first X-ray source SRC.1 and the first X-ray detector DTC.1 may also move on a common trajectory or on two separate elliptic trajectories. This yields an angle between the first projection direction $v_1$ and the second projection direction $v_2$ of $\varphi(v_1, v_2)=\omega \cdot \Delta t_1$, and an angle between the second projection direction $v_2$ and the third projection direction $v_3$ of $\varphi(v_2, v_3)=\omega \cdot \Delta t_2$.

Compared to the imaging geometry shown in FIG. 4, the imaging geometry shown in FIG. 5 can be achieved at a constant speed of rotation using just one X-ray source SRC.1 and one X-ray detector DTC.2. However, if the same X-ray projections XP.1, XP.2, XP.3 are to be generated, it is necessary on the one hand to reach a higher speed of rotation, while on the other hand the first X-ray source SRC.1 and the second X-ray source SRC.2 must perform a large number of revolutions around the examination volume VOL (in particular, approximately one revolution per four acquired X-ray projections XP.1, XP.2, XP.3). The imaging geometry shown in FIG. 5 is therefore advantageously realized via a computed tomography system, while the imaging geometry shown in FIG. 4 can also be realized in a C-arm X-ray device having two X-ray sources SRC.1, SRC.2 and two X-ray detectors DTC.1, DTC.2.

Figure 6:
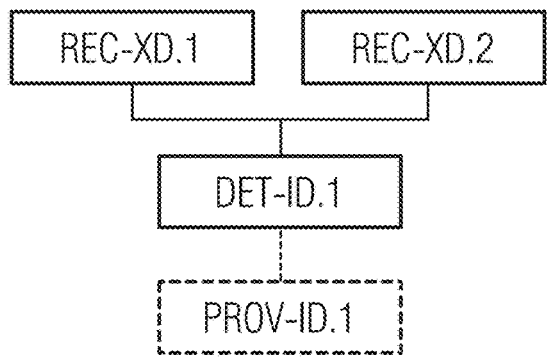
FIG. 6 shows a first example embodiment of a method for determining a three-dimensional image dataset of an examination volume.

FIG. 6 shows a first example embodiment of a method for determining a three-dimensional image dataset ID.1, ID.2 of an examination volume VOL.

The first steps of the first example embodiment shown are the receiving REC-XD.1 of a first X-ray dataset XD.1 of the examination volume VOL, the first X-ray dataset XD.1 comprising a two-dimensional first X-ray projection XP.1 of the examination volume VOL with respect to a first projection direction $v^{(1)}$, as well as the receiving REC-XD.2 of a second X-ray dataset XD.2 of the examination volume VOL, the second X-ray dataset XD.2 comprising a two-dimensional second X-ray projection XP.2 of the examination volume VOL with respect to a second projection direction $v^{(2)}$. The receiving REC-XD.1 of the first X-ray dataset XD.1 and the receiving REC-XD.2 of the second X-ray dataset are accomplished in particular via an interface IF.

If μ(x) denotes the X-ray absorption of the examination volume VOL at the spatial coordinate x, then the result yielded is $$b^{(1/2)}(y) \propto \int_{\Gamma\left\{y, v^{(1/2)}\right\}} \mu^{(1/2)}(x) dx$$

where $b^{(1)}(y)$ is the two-dimensional first X-ray projection XP.1 at the two-dimensional coordinate y of the X-ray detector DTC.1, DTC.2, $b^{(2)}(y)$ is the two-dimensional second X-ray projection at the two-dimensional coordinate y of the X-ray detector DTC.1, DTC.2, and $\Gamma(y, v)$ is the path from the X-ray source SRC.1, SRC.2 to the X-ray detector DTC.1, DTC.2 at the coordinate y when the projection direction corresponds to the angle v. In practical application there will of course be deviations due to inaccuracies and interference effects (e.g. a finite detector binning, scattered radiation or measurement inaccuracies).

In the example embodiment shown, the first projection direction $v^{(1)}$ and the second projection direction $v^{(2)}$ include an angle between 85° and 95°. This corresponds to the geometric arrangement shown in FIG. 4 or in FIG. 5. Alternatively, the angle may also be greater. Furthermore, the first X-ray dataset XD.1 comprises a first time point $t^{(1)}$, the first time point $t^{(1)}$ corresponding to the time point of the acquisition of the first X-ray projection XP.1, and the second X-ray dataset XD.2 comprises a second time point $t^{(2)}$, the second time point $t^{(2)}$ corresponding to the time point of the acquisition of the second X-ray projection XP.2. In this case, the time interval between the first time point $t^{(1)}$ and the second time point $t^{(2)}$ is less than 0.02 s. Alternatively, the time interval may also be greater. This corresponds to the data structure of the first X-ray dataset XD.1 and the second X-ray dataset XD.2 shown in FIG. 3.

A further step of the first example embodiment shown is a determining DET-ID.1 of a first three-dimensional image dataset ID.1 of the examination volume VOL based on the first X-ray projection XP.1 and the second X-ray projection XP.2. The determining DET-ID.1 of the first three-dimensional image dataset ID.1 is in this case accomplished in particular via a computing unit CU. The determining DET-ID.1 of the first three-dimensional image dataset ID.1 of the examination volume VOL may furthermore be based on a three-dimensional constraining image dataset CD of the examination volume.

Alternatively, a trained function may also be used which is based on the first X-ray projection XP.1, the second X-ray projection XP.2 as well as the first projection direction $v^{(1)}$ and the second projection direction $v^{(2)}$ as input data, and generates the first three-dimensional image dataset ID.1 of the examination volume as output data.

A further optional step of the first example embodiment shown is the provision PROV-ID.1 of the first three-dimensional image dataset ID.1, in particular via the interface IF. In this case, the first three-dimensional image dataset ID.1 is visualized via an output unit (for example a screen). Alternatively, the first three-dimensional image dataset ID.1 can also be transferred to a further system (for example to a "Picture Archiving and Communication System" ("PACS" for short)) or stored in a memory unit MU.

Figure 7:
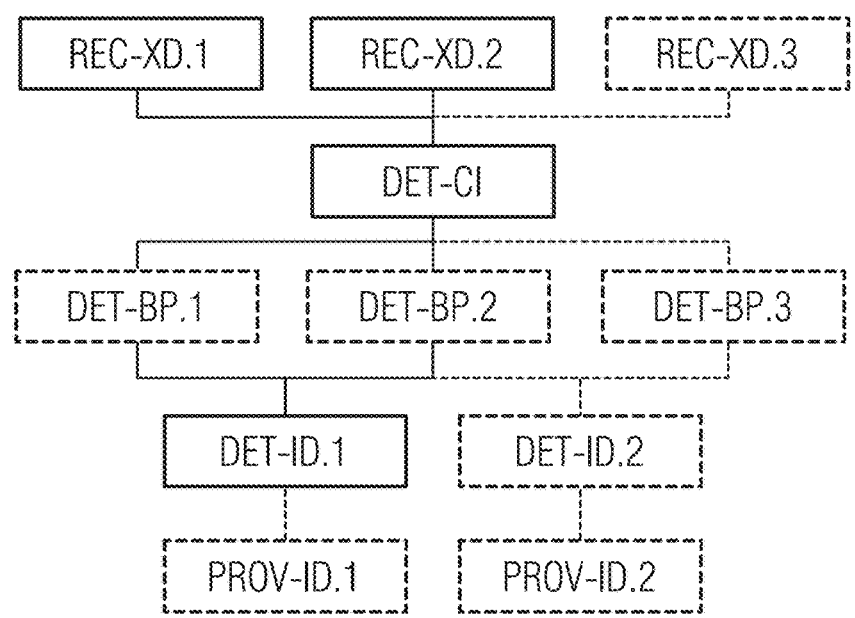
FIG. 7 shows a second example embodiment of a method for determining a three-dimensional image dataset of an examination volume.

FIG. 7 shows a second example embodiment of the method for determining a three-dimensional image dataset ID.1, ID.2 of an examination volume. The second example embodiment comprises all steps of the first example embodiment described and illustrated in FIG. 6. The respective steps may include in particular all advantages and embodiment variants described in relation to the first example embodiment.

An additional optional step of the second example embodiment is the receiving REC-XD.3 of a third X-ray dataset XD.3 of the examination volume VOL, the third X-ray dataset XD.3 comprising a two-dimensional third X-ray projection XP.1 of the examination volume VOL with respect to a third projection direction $v^{(3)}$. Furthermore, the third X-ray dataset XD.3 in this second example embodiment comprises a third time point $t^{(3)}$, the third time point $t^{(3)}$ corresponding to the time point of the acquisition of the third X-ray projection XP.3. In this case, the time interval between the second time point $t^{(2)}$ of the second X-ray dataset XD.2 and the third time point $t^{(3)}$ of the third X-ray dataset XD.3 is less than 0.02 s. Alternatively, the time interval may also be greater. This corresponds to the data structure of the first X-ray dataset XD.1, the second X-ray dataset XD.2 and the third X-ray dataset XD.3 shown in FIG. 3.

In the example embodiment shown, the second projection direction $v^{(2)}$ and the third projection direction $v^{(3)}$ include an angle between 85° and 95°. Alternatively, the angle may also be greater. Furthermore, the first projection direction $v^{(1)}$ and the third projection direction $v^{(3)}$ include an angle between 0° and 10°, in particular in the case in which the first X-ray projection XP.1 was acquired via a first X-ray source SRC.1 and a first X-ray detector DTC.1, and the second X-ray projection XP.2 was acquired via a second X-ray source SRC.2 and a second X-ray detector DTC.2, the first X-ray source SRC.1 and the second X-ray source SRC.2 being different. This corresponds to the geometric arrangement shown in FIG. 4.

Alternatively, the first projection direction $v^{(1)}$ and the third projection direction $v^{(3)}$ may also include an angle between 170° and 180°, in particular in the case in which the first X-ray projection XP.1 was acquired via a first X-ray source SRC.1 and a first X-ray detector DTC.1, and the second X-ray projection XP.2 was likewise acquired via the first X-ray source SRC.1 and the first X-ray detector DTC.1. This corresponds to the geometric arrangement shown in FIG. 5.

A further optional step of the second example embodiment is the determining DET-CI of a constraining image dataset CI via the computing unit CU. In this example embodiment, the determining DET-CI of the constraining image dataset CI is based on the first X-ray dataset XD.1, the second X-ray dataset XD.2 and the third X-ray dataset XD.3. Alternatively, the determining DET-CI of the constraining image dataset CI may also be based only on the first X-ray dataset XD.1 and/or the second X-ray dataset XD.3. For example, the constraining image dataset CI can be determined by applying a trained function to the first X-ray dataset XD.1, the second X-ray dataset XD.2 and the third X-ray dataset XD.3, as is described in the European patent application 18182251.1, the entire contents of which are hereby incorporated herein by reference, or in the German patent applications 102019200270.6 and 102019200269.2, the entire contents of each of which are hereby incorporated herein by reference. In particular, the constraining image dataset CI may be based on further X-ray projections or X-ray datasets of the examination volume VOL.

In this second example embodiment, the constraining image dataset CI is a three-dimensional image dataset comprising voxels, each voxel being assigned either a first value or a second value. In particular, in this second example embodiment, the value of a voxel is $C_{ijk}=1$ if the voxel having the indices i, j and k images a vessel VES.1, VES.2 in the examination volume VOL, and the value of a voxel is $C_{ijk}=0$ if the voxel having the indices i, j and k images no vessel VES.1, VES.2 in the examination volume VOL.

Alternatively to the discrete description, the constraining image dataset CI may also be described by way of a continuous function C(x), where C(x)=1 if the coordinate x corresponds to a vessel VES.1, VES.2 in the examination volume VOL, and where C(x)=0 if the coordinate x corresponds to no vessel VES.1, VES.2 in the examination volume.

Further optional steps of the second example embodiment are the determining DET-BP.1 of a first three-dimensional back-projection dataset BP.1 based on the first X-ray dataset XD.1 and on the constraining image dataset CI, the determining DET-BP.2 of a second three-dimensional back-projection dataset BP.2 based on the second X-ray dataset XD.2 and on the constraining image dataset CI, and the determining DET-BP.3 of a third three-dimensional back-projection dataset BP.3 based on the third X-ray dataset XD.3 and on the constraining image dataset CI.

In this example embodiment, the back-projection datasets BP.1, BP.2, BP.3 are determined using a multiplicative back-projection which is given by the following functional relationship:

$$P^{(i)}(x) = \frac{C(x) \cdot b^{(i)}(y(x))}{\int_{\Gamma(y(x), v^{(i)})} C(l) dl}$$

where x is a three-dimensional spatial coordinate, and $P^{(i)}$ is a back-projection dataset BP.1, BP.2, BP.3. The two-dimensional coordinate y(x) corresponds to the coordinate that is yielded from the projection of the three-dimensional coordinate x with respect to the projection direction $v^{(i)}$ onto the X-ray detector DTC.1, DTC.2. The path $\Gamma(y(x), v^{(i)})$ corresponds to all three-dimensional coordinates that are mapped by way of the X-ray projection with respect to the projection direction $v^{(i)}$ onto the two-dimensional coordinate y(x). Clearly, therefore, the intensity values of the two-dimensional coordinates y(x) are uniformly distributed to the voxels of the constraining image dataset C(x) along the projection direction $v^{(i)}$ in which C(x)=1.

The determining DET-ID.1 of the first three-dimensional image dataset ID.1 of the examination volume VOL is based in this example embodiment on the first back-projection dataset BP.1 and the second back-projection dataset BP.2. In particular, as a result of pixel-wise multiplication $B^{(1)}(x) = P^{(1)}(x) \cdot P^{(2)}(x)$ of the first back-projection dataset BP.1 and the second back-projection dataset BP.2, the first three-dimensional image dataset ID.1 is based on the respective back-projection datasets BP.1, BP.2.

The second example embodiment shown also optionally comprises a determining DET-ID.2 of a second three-dimensional image dataset ID.2 of the examination volume based on the second X-ray projection XP.2 and the third X-ray projection. XP.3. In this second example embodiment, the second three-dimensional image dataset ID.2 is based in addition in particular on the constraining image dataset CI in that it is based on the second back-projection dataset BP.2 and the third back-projection dataset BP.3. In particular, as a result of pixel-wise multiplication $B^{(2)}(x) = P^{(2)}(x) \cdot P^{(3)}(x)$ of the second back-projection dataset BP.2 and the third back-projection dataset BP.3, the second three-dimensional image dataset ID.2 is based on the respective back-projection datasets BP.2, BP.3.

A further optional step of the illustrated second example embodiment is the provision PROV-ID.2 of the second three-dimensional image dataset ID.2, in particular via the interface IF. In this case, the second three-dimensional image dataset ID.2 is visualized via an output unit (for example a screen). Alternatively, the second three-dimensional image dataset ID.2 may also be transferred to a further system (for example to a "Picture Archiving and Communication System" ("PACS" for short)) or stored in a memory unit MU.

Figure 8:
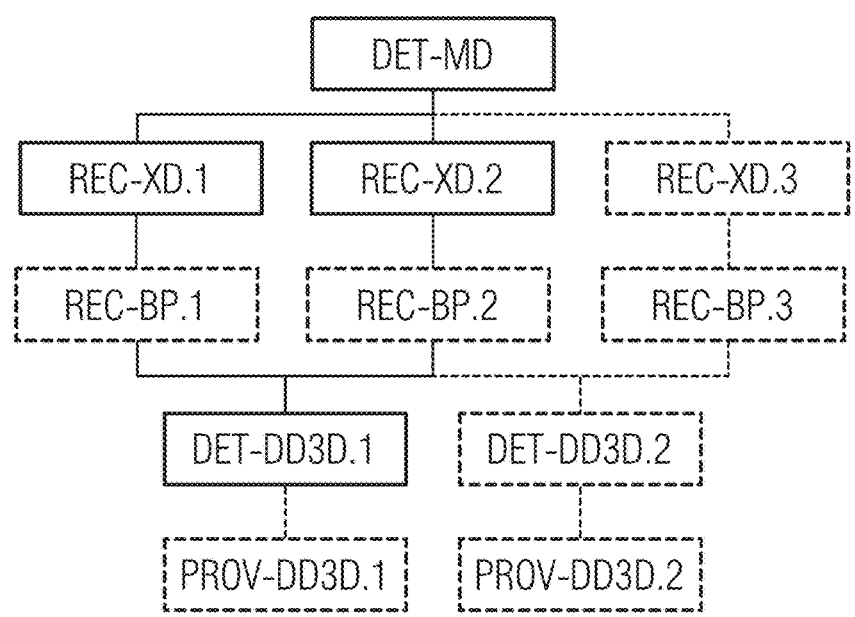
FIG. 8 shows a third example embodiment of a method for determining a three-dimensional image dataset of an examination volume.

FIG. 8 shows a third example embodiment of the method for determining a three-dimensional image dataset ID.1, ID.2 of an examination volume VOL. The third example embodiment comprises all steps of the second example embodiment described and illustrated in FIG. 7. The respective steps may include in particular all advantages and embodiment variants described in relation to the second example embodiment.

In contrast to the second example embodiment, the constraining image dataset CI is in this case not based on the first X-ray dataset XD.1, the second X-ray dataset XD.2 or the third X-ray dataset XD.3, but is received via the interface IF.

Figure 9:
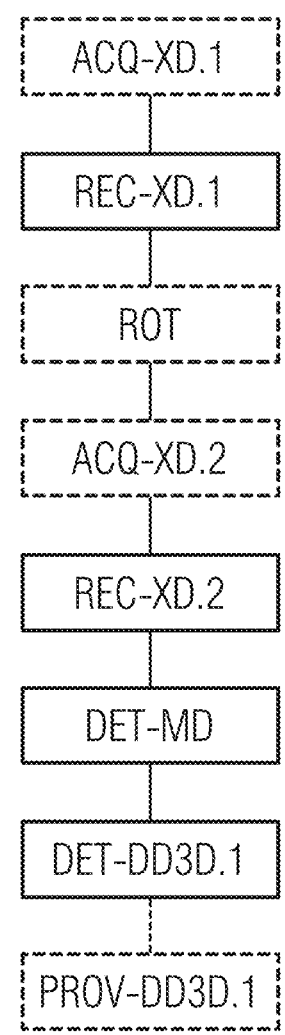
FIG. 9 shows a fourth example embodiment of a method for determining a three-dimensional image dataset of an examination volume.

FIG. 9 shows a fourth example embodiment of the method for determining a three-dimensional image dataset ID.1, ID.2 of an examination volume VOL. The third example embodiment comprises all steps of the first example embodiment described and illustrated in FIG. 6. The respective steps may in particular include all advantages and embodiment variants described with respect to the first example embodiment. The fourth example embodiment relates in this case in particular to the geometric arrangement shown in FIG. 5.

The fourth example embodiment furthermore comprises an optional acquisition ACQ-XD.1 of the first X-ray dataset XD.1 via a first X-ray source SRC.1 and a first X-ray detector DTC.1 of an X-ray device XSYS, a first rotation ROT-1 of the first X-ray detector DTC.1 and the first X-ray source SRC.1 around the examination volume VOL, and an acquisition ACQ-XD.2 of the second X-ray dataset CD.2 via the first X-ray source SRC.1 and the first X-ray detector DTC.1 of the X-ray device XSYS.

In this case, the acquisition ACQ-XD.1 of the first X-ray dataset XD.1 takes place before the receiving REC-XD.1 of the first X-ray dataset XD.1, and the acquisition ACQ-XD.2 of the second X-ray dataset XD.2 takes place before the receiving REC-XD.2 of the second X-ray dataset. The first rotation ROT-1 of the first X-ray source SRC.1 and the first X-ray detector takes place between the acquisition ACQ-XD.1 of the first X-ray dataset XD.1 and the acquisition ACQ-XD.2 of the second X-ray dataset XD.2. In this example embodiment, the acquisition ACQ-XD.1 of the first X-ray dataset XD.1 takes place before the acquisition ACQ-XD.2 of the second X-ray dataset XD.2. Alternatively, the acquisition ACQ-XD.1 of the first X-ray dataset XD.1 may also take place concurrently with or after the acquisition ACQ-XD.2 of the second X-ray dataset.

The first rotation ROT-1 is performed through an angle corresponding to the angle between the first projection direction $v^{(1)}$ and the second projection direction $v^{(2)}$. The first X-ray source SRC.1 and the first X-ray detector DTC.1 in this case rotate in particular simultaneously around the examination volume VOL, and in particular around a common axis of rotation.

Figure 10:
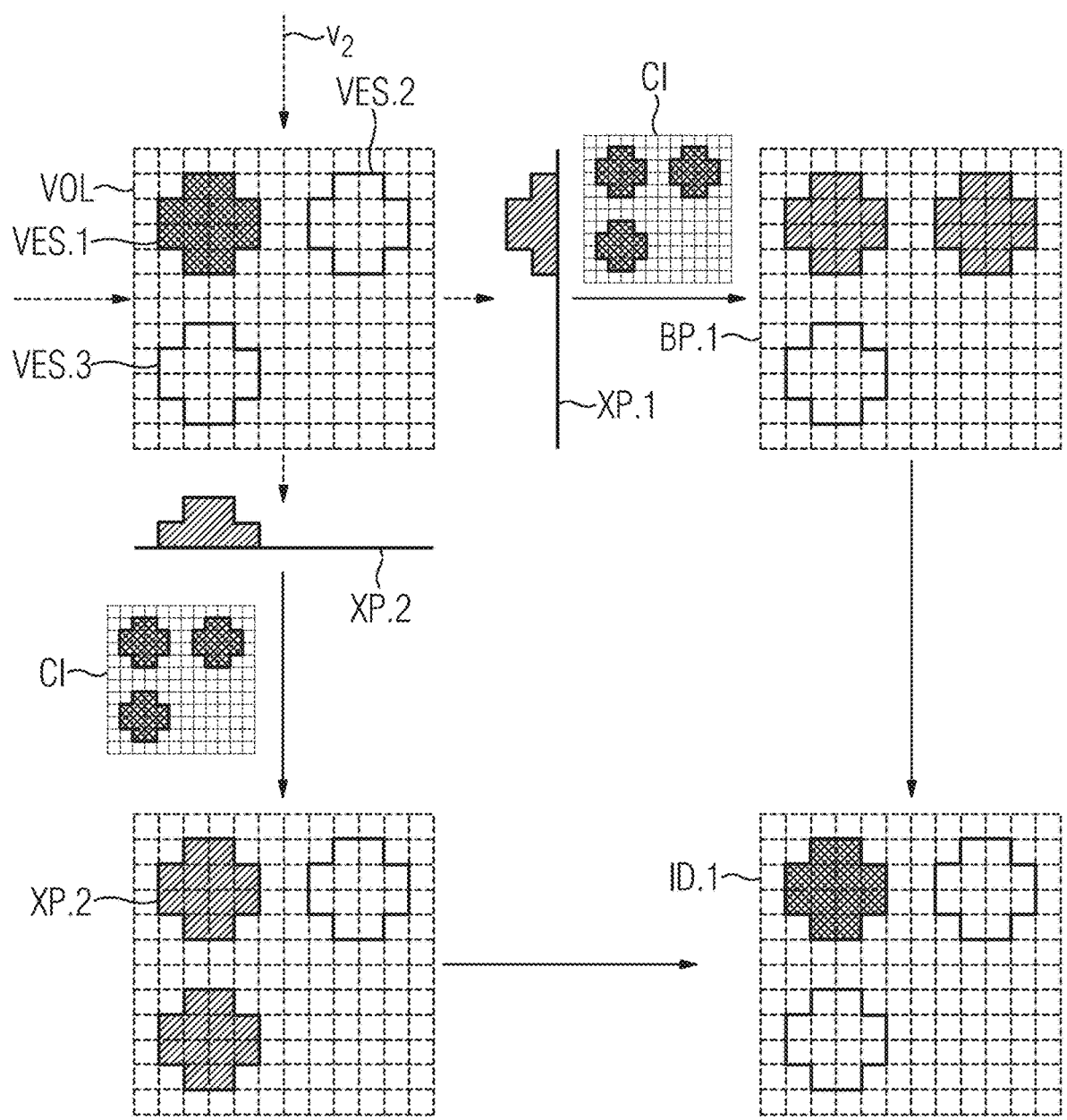
FIG. 10 shows a detailed explanation of the step of determining the first three-dimensional image dataset.

FIG. 10 shows a detailed explanation of the step of determining DET-DI.1 the first three-dimensional image dataset DI.1 of the foregoing example embodiments. In this case, in the illustration presented in FIG. 10, the examination volume VOL as well as all image datasets ID.1 and X-ray projections XP.1, XP.2 are represented with one dimension less than they actually have.

The illustration in FIG. 10 shows an examination volume VOL containing three vessels VES.1, VES.2, VES.3. In this case, the first vessel VES.1 is filled with contrast agent, and the second vessel VES.2 and the third vessel are not filled with contrast agent. Of the examination volume VOL, a first X-ray projection XP.1 is acquired with respect to the first projection direction $v_1$ and a second X-ray projection XP.2 is acquired with respect to a second projection direction $v_2$.

In this example, the first projection direction $v_1$ is arranged in such a way that it is not possible to establish, based on the first X-ray projection XP.1 alone, whether the first vessel VES.1 and/or the second vessel VES.2 contain contrast agent or, as the case may be, which contrast agent density is present, since the first vessel VES.1 and the second vessel VES.2 overlay or overlap each other with respect to the first projection direction $v_1$. Therefore, if a first back-projection dataset BP.1 is generated based solely on the first X-ray projection XP.1 and the constraining image dataset CI, the first back-projection dataset BP.1 is either rejected as unreliable on account of the overlapping or, as in the illustrated example embodiment, has incorrect values for the X-ray absorption.

Furthermore, the second projection direction $v_2$ is arranged in such a way that it is not possible to establish, based on the second X-ray projection XP.2 alone, whether the first vessel VES.1 and/or the third vessel VES.3 contain contrast agent or, as the case may be, which contrast agent density is present, since the first vessel VES.1 and the third vessel VES.3 overlay or overlap each other with respect to the second projection direction $v_2$. Therefore, if a second back-projection dataset BP.2 is generated based solely on the second X-ray projection XP.2 and the constraining image dataset CI, the second back-projection dataset BP.2 is either rejected as unreliable on account of the overlapping or, as in the illustrated example embodiment, has incorrect values for the X-ray absorption.

However, by multiplication of the first back-projection dataset BP.1 and the second back-projection dataset XP.2, a first three-dimensional image dataset XD.1 is obtained which correctly images the contrast agent distribution in the examination volume. In particular, non-zero intensity values are assigned only to those pixels or voxels in the first three-dimensional image dataset ID.1 whose corresponding pixels or voxels are also assigned non-zero intensity values both in the first back-projection dataset BP.1 and in the second back-projection dataset BP.2.

Figure 11:
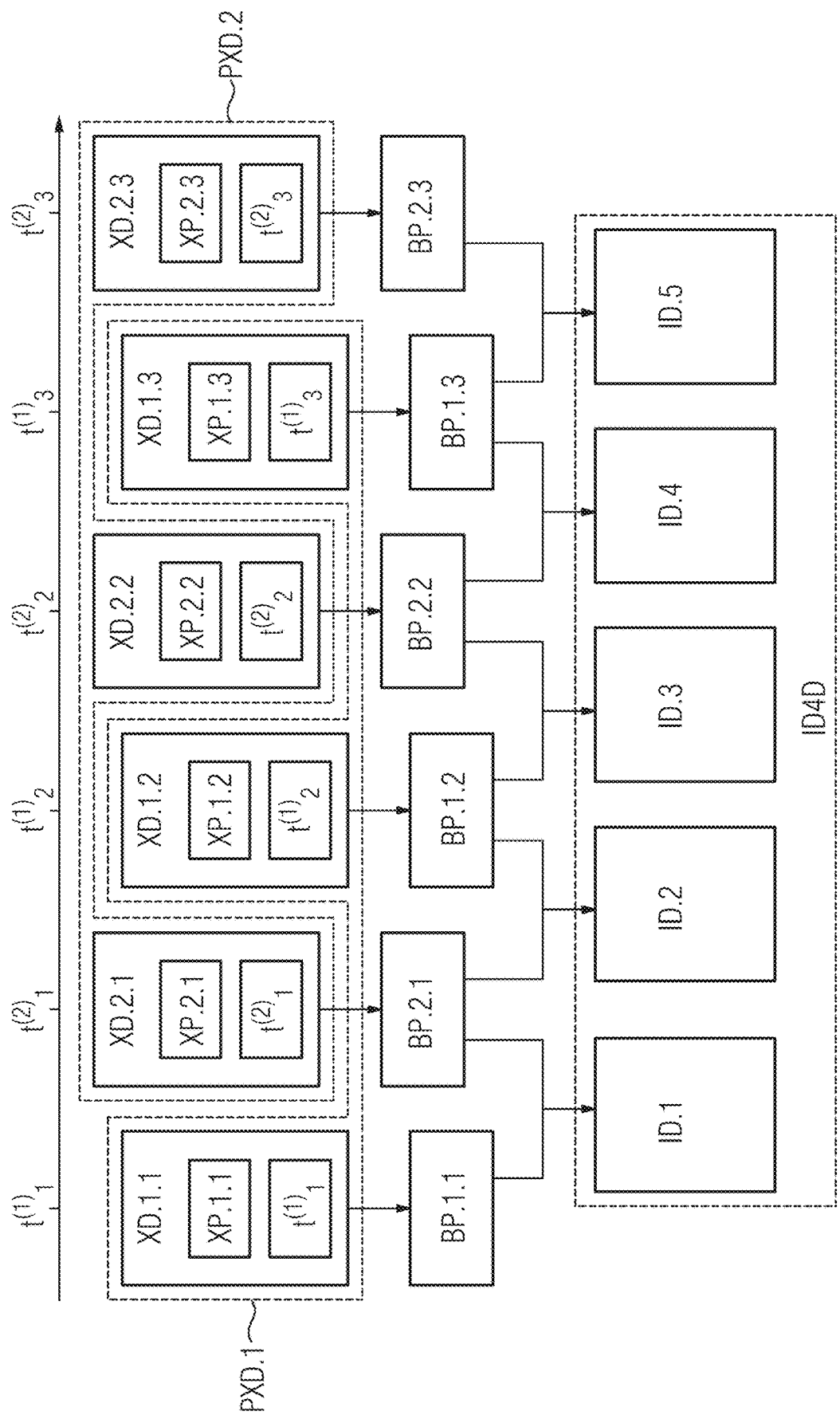
FIG. 11 shows first and second X-ray datasets.

FIG. 11 shows first X-ray datasets XD.1.1, ..., XD.1.3, and second X-ray datasets XD.2.1, ..., XD.2.4. In this case, each of the first X-ray datasets XD.1.1, ..., XD.1.3 comprises an X-ray projection XP.1.1, ..., XP.1.3 of an examination volume VOL with respect to a projection direction $v^{(1)}_1, \ldots, v^{(1)}_3$, as well as a time point $t^{(1)}_1, \ldots, t^{(1)}_3$, the time point $t^{(1)}_1, \ldots, t^{(1)}_3$ corresponding to the time point of the acquisition of the corresponding X-ray projection XP.1.1, ..., XP.1.3. Furthermore, each of the second X-ray datasets XD.2.1, ..., XD.2.3 comprises an X-ray projection XP.2.1, ..., XP.2.3 of the examination volume VOL with respect to a projection direction $v^{(2)}_1, \ldots, v^{(2)}_3$, as well as a time point $t^{(2)}_1, \ldots, t^{(2)}_3$, the time point $t^{(2)}_1, \ldots, t^{(2)}_3$ corresponding to the time point of the acquisition of the corresponding X-ray projection XP.2.1, ..., XP.2.3.

The first X-ray datasets XD.1.1, ..., XD.1.3 may be referred to in particular as a first plurality or first set PXD.1 of X-ray datasets, and the second X-ray datasets XD.2.1, ..., XD.2.3 may be referred to in particular as a second plurality or second set PXD.2 of X-ray datasets.

In the example embodiment shown, both the first X-ray datasets XD.1.1, ..., XD.1.3 and the second X-ray datasets XD.2.1, ..., XD.2.3 each comprise three X-ray datasets XD.1.1, ..., XD.1.3, XD.2.1, ..., XD.2.3. Typically, both the first X-ray datasets XD.1.1, ..., XD.1.3 and the second n X-ray datasets XD.2.1, ..., XD.2.3 comprise a greater number of X-ray datasets XD.1.1, ..., XD.1.3, XD.2.1, ..., XD.2.3. In particular, the number of first X-ray datasets XD.1.1, ..., XD.1.3 and the number of second X-ray datasets XD.2.1, ..., XD.2.3 may also be different.

In the example embodiment shown, all the time points $t^{(1)}_1, \ldots, t^{(1)}_3, t^{(2)}_1, \ldots, t^{(2)}_3$ are pairwise distinct. Furthermore, the notation in this example embodiment is chosen such that the time point $t^{(2)}_i$ is located after the time point $t^{(1)}_i$ in time and before the time point $t^{(1)}_{i+1}$ in time. Alternatively, the time point $t^{(2)}_i$ may also be located after the time point $t^{(1)}_{i+k}$ in time and before the time point $t^{(1)}_{i+1+k}$ in time, where k is an arbitrary negative or positive whole number.

The time points $t^{(1)}_1, \ldots, t^{(1)}_3$ of the first X-ray datasets XD.1.1, XD.1.3 have a constant time interval, i.e. $t^{(1)}_{i+1} - t^{(1)}_i = \Delta t$, and the time points $t^{(2)}_1, \ldots, t^{(2)}_3$ of the second X-ray datasets XD.2.1, ..., XD.2.3 have the same constant time interval, i.e. $t^{(2)}_{i+1} - t^{(2)}_i = \Delta t$. In particular, the time points $t^{(1)}_1, \ldots, t^{(1)}_3, t^{(2)}_1, \ldots, t^{(2)}_3$ may be chosen such that $t^{(2)}_i = t^{(1)}_i + a \cdot (t^{(1)}_{i+1} - t^{(1)}_i) = t^{(1)}_i + a \Delta t$, and in particular a may be chosen such that a=0.5, in which case the time points $t^{(2)}_1, \ldots, t^{(2)}_3$ of the second X-ray datasets XD.2.1, ..., XD.2.3 are in each case the midpoint in time between two time points $t^{(1)}_1, \ldots, t^{(1)}_3$ of the first X-ray datasets XD.1.1, XD.1.3.

In this example embodiment, the time interval $\Delta t$ is less than 5 s, in particular less than 2 s, in particular less than 1 s, in particular less than 0.5 s, in particular less than 0.1 s, and in particular less than 0.02 s. In particular, it also holds that $\Delta t_1 = \Delta t_2 = \Delta t$.

The X-ray datasets XD.1.1, ..., XD.1.3, XD.2.1, ..., XD.2.3 may also comprise further data, for example the X-ray voltage or the X-ray current used for the X-ray projection XP.1.1, ..., XP.1.3, XP.2.1, ..., XP.2.3, or other relevant parameters for the X-ray projection. The X-ray datasets XD.1.1, ..., XD.1.3, XD.2.1, ..., XD.2.3 may also comprise in particular the projection direction $v^{(1)}_1, \ldots, v^{(1)}_3, v^{(2)}_1, \ldots, v^{(2)}_3$ of the associated X-ray projection XP.1.1, ..., XP.1.3, XP.2.1, ..., XP.2.3.

Figure 12:
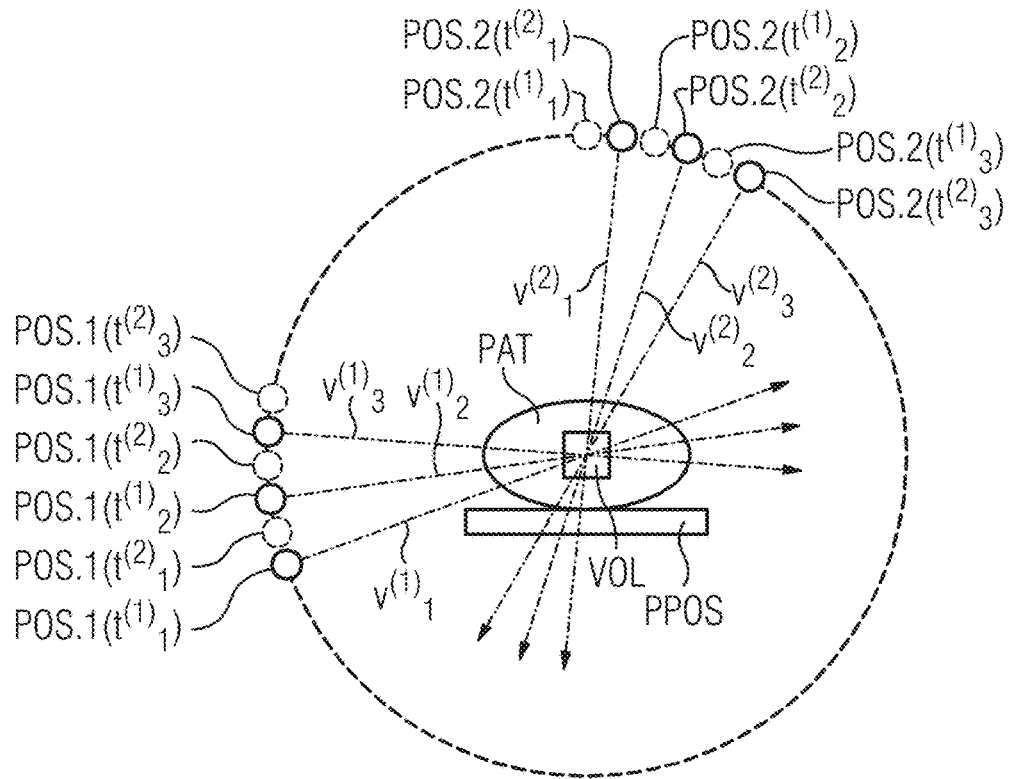
FIG. 12 shows a first example embodiment of a geometric arrangement of an acquisition of first X-ray datasets and second X-ray datasets.

FIG. 12 shows a first example embodiment of a geometric arrangement of an acquisition of first X-ray datasets XD.1.1, ..., XD.1.3 and second X-ray datasets XD.2.1, ..., XD.2.3.

The first example embodiment shown in FIG. 12 may in this case be interpreted in particular as an extension of the example embodiment shown in FIG. 4 in which more X-ray datasets XD.1.1, ..., XD.1.3, XD.2.1, ..., XD.2.3 are acquired.

The examination volume VOL is in this case part of a patient PAT that is supported on a patient support and positioning device PPOS. The first X-ray datasets XD.1.1, ..., XD.1.3 are in this case determined via a first X-ray source SRC.1 and a first X-ray detector DTC.1, the second X-ray datasets XD.2.1, ..., XD.2.3 via a second X-ray source SRC.2 and a second X-ray detector DTC.2.

Also shown in FIG. 12 are the positions POS.1$(t^{(1/2)}_i)$ of the first X-ray source SRC.1 and the positions POS.2$(t^{(1/2)}_i)$ of the second X-ray source at a time point $t^{(1)}_i$ of the first X-ray datasets XD.1.1, ..., XD.1.3 and a time point $t^{(2)}_i$ of the second X-ray datasets XD.2.1, ..., XD.2.3, respectively.

For clarity of illustration reasons, the positions of the first X-ray detector DTC.1 and the second X-ray detector DTC.2 have not been depicted, the latter being located in each case on the opposite side of the examination volume VOL orthogonally to the respective projection direction $v^{(1)}_1, \ldots, v^{(1)}_3, v^{(2)}_1, \ldots, v^{(2)}_3$. The relative arrangement of the time points $t^{(1)}_1, \ldots, t^{(1)}_3, t^{(2)}_1, \ldots, t^{(2)}_3$ may be derived by reference to FIG. 11.

In this example embodiment, the projection directions $v^{(1)}_i$ and $v^{(2)}_i$ and the projection directions $v^{(2)}_i$ and $v^{(1)}_{i+1}$ include, respectively, an angle $\varphi(v^{(1)}_i, v^{(2)}_i)$ and $\varphi(v^{(2)}_i, v^{(1)}_{i+1})$ between 45° and 135°, in particular an angle between 60° and 120°, in particular an angle between 80° and 100°, in particular an angle between 85° and 95°.

The angle between the respective projection directions $v^{(1)}_1, \ldots, v^{(1)}_3, v^{(2)}_1, \ldots, v^{(2)}_3$ is achieved in this example embodiment in that both the first X-ray source SRC.1, simultaneously with the first X-ray detector DTC.1, and the second X-ray source SRC.2, simultaneously with the second X-ray detector DTC.2, rotate around the examination volume VOL, in particular at a constant angular velocity $\omega$ and on a circular trajectory in each case. This yields the angles $\varphi(v^{(1)}_i, v^{(2)}_i) = \varphi_0 + \omega \cdot \Delta t_1$ and $\varphi(v^{(2)}_i, v^{(1)}_{i+1}) = \varphi_0 + \omega \cdot \Delta t_2$, where $\varphi_0$ is the constant angle between the direction vector from the first X-ray source SRC.1 to the first X-ray detector DTC.1 and the direction vector from the second X-ray source SRC.2 to the second X-ray detector DTC.2. Advantageously, the angle chosen is $\varphi_0 = 900$.

Figure 13:
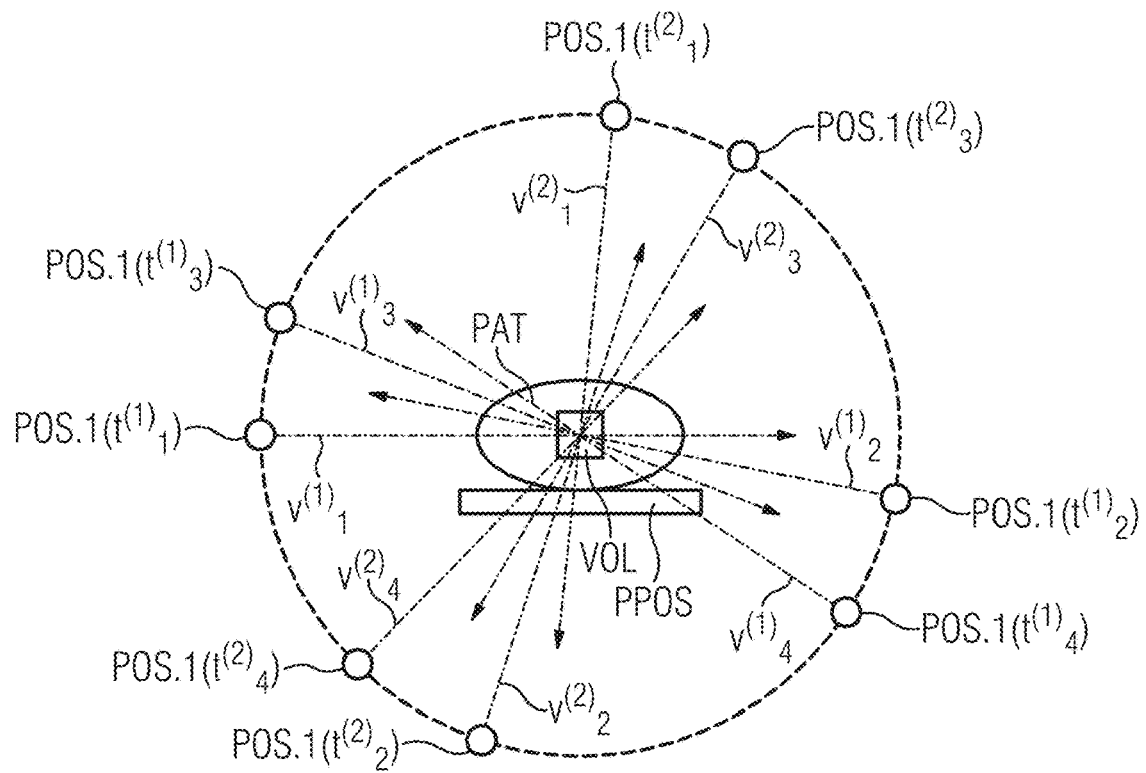
FIG. 13 shows a first example embodiment of a geometric arrangement of an acquisition of first X-ray datasets and second X-ray datasets.

FIG. 13 shows a second example embodiment of a geometric arrangement of an acquisition of first X-ray datasets XD.1.1, ..., XD.1.3 and second X-ray datasets XD.2.1, ..., XD.2.3. The first X-ray datasets XD.1.1, ..., XD.1.3 and the second X-ray datasets XD.2.1, ..., XD.2.3 are in this case acquired via a first X-ray source SRC.1 and a first X-ray detector DTC.1.

The second example embodiment shown in FIG. 12 may in this case be interpreted in particular as an extension of the example embodiment shown in FIG. 5 in which more X-ray datasets XD.1.1, ..., XD.1.3, XD.2.1, ..., XD.2.3 are acquired.

Also shown in FIG. 13 are the positions POS.1($t^{(1/2)}_i$) of the first X-ray source POS.1 at a time point $t^{(1)}_i$ of the first X-ray datasets XD.1.1, ..., XD.1.3 or, as the case may be, at a time point $t^{(2)}_i$ of the second X-ray datasets XD.2.1, ..., XD.2.3. For clarity of illustration reasons, the positions of the first X-ray detector DTC.1 have not been depicted, the latter being located in each case on the opposite side of the examination volume VOL orthogonally to the respective projection direction $v^{(1)}_1, \ldots, v^{(1)}_3, v^{(2)}_1, \ldots, v^{(2)}_3$. The relative arrangement of the time points $t^{(1)}_1, \ldots, t^{(1)}_3, t^{(2)}_1, \ldots, t^{(2)}_3$ may be derived by reference to FIG. 11.

In this example embodiment, the projection directions $v^{(1)}_i$ and $v^{(2)}_i$ and the projection directions $v^{(2)}_i$ and $v^{(1)}_{i+1}$ include, respectively, an angle $\varphi(v^{(1)}_i, v^{(2)}_i)$ and $\varphi(v^{(2)}_i, v^{(1)}_{i+1})$ between 45° and 135°, in particular an angle between 60° and 120°, in particular an angle between 80° and 100°, in particular an angle between 85° and 95°.

The angle between the respective projection directions $v^{(1)}_1, \ldots, v^{(1)}_3, v^{(2)}_1, \ldots, v^{(2)}_3$ is achieved in this example embodiment in that the first X-ray source SRC.1 rotates simultaneously with the first X-ray detector DTC.1, in particular at a constant angular velocity $\omega$ and on a circular trajectory. This yields the angles $\varphi(v^{(1)}_i, v^{(2)}_i) = \omega \cdot \Delta t_1$ and $\varphi(v^{(2)}_i, v^{(1)}_{i+1}) = \omega \cdot \Delta t_2$.

Figure 14:
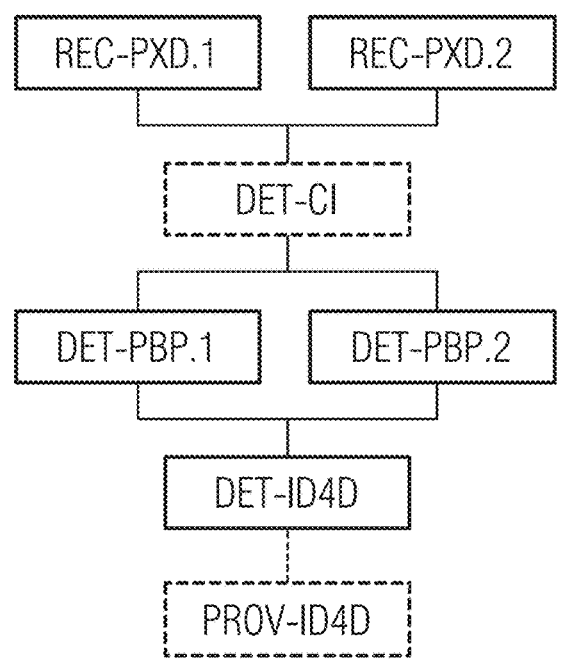
FIG. 14 shows a first example embodiment of a method for determining a four-dimensional image dataset of an examination volume.

FIG. 14 shows a first example embodiment of a method for determining a four-dimensional image dataset ID4D of an examination volume VOL.

In this first example embodiment, the method comprises the receiving REC-PXD.1 of first X-ray datasets XD.1.1, ..., XD.1.3 of the examination volume VOL via an interface, each X-ray dataset of the first X-ray datasets XD.1.1, ..., XD.1.3 comprising a two-dimensional X-ray projection XP.1.1, ..., XP.1.3 of the examination volume VOL with respect to a projection direction $v^{(1)}_1, \ldots, v^{(1)}_3$. The method further comprises the receiving REC-PXD.2 of second X-ray datasets XD.2.1, ..., XD.2.3 of the examination volume VOL via the interface, each X-ray dataset of the second X-ray datasets XD.2.1, ..., XD.2.3 comprising a two-dimensional X-ray projection XP.2.1, ..., XP.2.3 of the examination volume VOL with respect to a projection direction $v^{(2)}_1, \ldots, v^{(2)}_3$.

The first X-ray datasets XD.1.1, ..., XD.1.3 may also be referred to as a first plurality PXD.1 of X-ray datasets, and the further X-ray datasets XD.2.1, ..., XD.2.3 may also be referred to as a second plurality PXD.2 of X-ray datasets.

An optional step of the first example embodiment is the determining DET-CI of a three-dimensional constraining image dataset CI via a computing unit. In this example embodiment, the first X-ray datasets XD.1.1, ..., XD.1.3 and the second X-ray datasets XD.2.1, ..., XD.2.3 are difference image datasets in each case, and the three-dimensional constraining image dataset CI can be determined via a reconstruction of the first X-ray datasets XD.1.1, ..., XD.1.3 and the second X-ray datasets XD.2.1, ..., XD.2.3 as well as by a subsequent segmentation. Alternatively, the constraining image dataset may also be received via the interface.

Further optional steps of the first example embodiment are the determining DET-PBP.1 of first three-dimensional back-projection datasets BP.1.1, ..., BP.1.3 based on the first X-ray datasets XD.1.1, ..., XD.1.3 and on the constraining image dataset CI via the computing unit CU, as well as the determining DET-PBP.2 of second three-dimensional back-projection datasets BP.2.1, ..., BP.2.3 based on the second X-ray datasets XD.2.1, ..., XD.2.3 and on the constraining image dataset CI. The constraining image datasets BP.1.1, ..., BP.1.3, BP.2.1, ..., BP.2.3 are in this case determined analogously to the procedure described in relation to FIG. 7.

A further step of the first example embodiment shown is the determining DET-ID4D of a four-dimensional image dataset ID4D based on the first X-ray datasets XD.1.1, ..., XD.1.3 as well as on the second X-ray datasets XD.2.1, ..., XD.2.3.

In this case, the four-dimensional image dataset ID4D comprises a plurality of three-dimensional image datasets ID.1, ..., ID.5, each of the three-dimensional image datasets ID.1, ..., ID.5 being based on a first X-ray dataset of the first X-ray datasets XD.1.1, ..., XD.1.3 and on a second X-ray dataset of the second X-ray datasets XD.2.1, ..., XD.2.3. In particular, each first X-ray dataset of the first X-ray datasets XD.1.1, ..., XD.1.3 serves in this case as a basis for at most two of the three-dimensional image datasets ID.1, ..., ID.5, and each second X-ray dataset of the second X-ray datasets XD.2.1, ..., XD.2.3 serves as a basis for at most two of the three-dimensional image datasets ID.1, ..., ID.5. The schematic assignment of the first X-ray datasets XD.1.1, ..., XD.1.3, the second X-ray datasets XD.2.1, ..., XD.2.3 and the three-dimensional image datasets ID.1, ..., ID.5 corresponds to the assignment shown in FIG. 11.

In particular, each of the three-dimensional image datasets ID.1, ..., ID.5 is based on a first X-ray dataset of the first X-ray datasets XD.1.1, ..., XD.1.3 in that the three-dimensional image dataset ID.1, . . . , ID.5 is based on a first three-dimensional back-projection dataset BP.1.1, . . . , BP.1.3, the first respective first three-dimensional back-projection dataset BP.1.1, . . . , BP.1.3 being based on the first X-ray dataset and the constraining image dataset CI. In particular, each of the three-dimensional image datasets ID.1, . . . , ID.5 is based on a second X-ray dataset of the second X-ray datasets XD.2.1, . . . , XD.2.3 in that the three-dimensional image dataset ID.1, . . . , ID.5 is based on a second three-dimensional back-projection dataset BP.2.1, . . . , BP.2.3, the first respective second three-dimensional back-projection dataset BP.2.1, . . . , BP.2.3 being based on the second X-ray dataset and the constraining image dataset CI.

If, in this first example embodiment, a first X-ray dataset of the first X-ray datasets XD.1.1, . . . , XD.1.3 and a second X-ray dataset of the second X-ray datasets XD.2.1, . . . , XD.2.2 are the basis of one of the three-dimensional image datasets XD.1, . . . , XD.5, then the projection direction $v^{(1)}_i, \ldots, v^{(1)}_3$ of the X-ray projection XP.1.1, . . . , XP.1.3 of the first X-ray dataset and the projection direction $v^{(2)}_1, \ldots, v^{(2)}_3$ of the X-ray projection XP.2.1, . . . , XP.2.3 of the second X-ray dataset generally include an angle between 45° and 135°, in particular an angle between 60° and 120°, in particular an angle between 80° and 100°, and, in this first example embodiment, in particular an angle between 85° and 95°.

In this first example embodiment, the first X-ray datasets XD.1.1, . . . , XD.1.3 further comprise first time points $t^{(1)}_1, \ldots, t^{(1)}_3$ corresponding to the time point of the acquisition of the respective X-ray projection XP.1.1, . . . , XP.1.3, and the second X-ray datasets XD.2.1, . . . , XD.2.3 comprise second time points $t^{(2)}_1, \ldots, t^{(2)}_3$ corresponding to the time point of the acquisition of the respective X-ray projection XP.2.1, . . . , XP.2.3.

If, in this first example embodiment, a first X-ray dataset of the first X-ray datasets XD.1.1, . . . , XD.1.3 and a second X-ray dataset of the second X-ray datasets XD.2.1, . . . , XD.2.2 are the basis of one of the three-dimensional image datasets XD.1, . . . , XD.5, then the time interval between the time point $t^{(1)}_1, \ldots, t^{(1)}_3$ of the first X-ray dataset and the time point $t^{(2)}_1, \ldots, t^{(2)}_3$ of the second X-ray dataset is generally less than 5 s, in particular less than 2 s, in particular less than 1 s, in particular less than 0.5 s, in particular less than 0.1 s, and, in this first example embodiment, in particular less than 0.02 s.

If, in this first example embodiment, a first X-ray dataset of the first X-ray datasets XD.1.1, . . . , XD.1.3 and a second X-ray dataset of the second X-ray datasets XD.2.1, . . . , XD.2.2 are the basis of one of the three-dimensional image datasets XD.1, . . . , XD.5, and if, at the same time, a third X-ray dataset of the first X-ray datasets XD.1.1, . . . , XD.1.3 and the second X-ray dataset of the second X-ray datasets XD.2.1, . . . , XD.2.2 are the basis of another of the three-dimensional image datasets XD.1, . . . , XD.5, then the time point $t^{(2)}_1, \ldots, t^{(2)}_3$ assigned to the second X-ray dataset is in particular the midpoint in time between the time point $t^{(1)}_1, \ldots, t^{(1)}_3$ assigned to the first X-ray dataset and the time point $t^{(1)}_1, \ldots, t^{(1)}_3$ assigned to the third X-ray dataset.

If, in this first example embodiment, a first X-ray dataset of the first X-ray datasets XD.1.1, . . . , XD.1.3 and a second X-ray dataset of the second X-ray datasets XD.2.1, . . . , XD.2.2 are the basis of one of the three-dimensional image datasets XD.1, . . . , XD.5, then in particular the midpoint in time between the time point $t^{(1)}_1, \ldots, t^{(1)}_3$ of the first X-ray dataset and the time point $t^{(2)}_i, \ldots, t^{(2)}_3$ of the second X-ray dataset is assigned as time coordinate to said three-dimensional image dataset XD.1, . . . , XD.5.

In this example embodiment, the four-dimensional image dataset ID4D then comprises the temporally arranged three-dimensional image datasets ID.1, . . . , ID.5, and is accordingly embodied as spatially three-dimensional and temporally one-dimensional.

A further optional step of the first example embodiment shown is the provision PROV-ID4D of the four-dimensional image dataset ID4D, in particular via the interface IF. In this case, the four-dimensional image dataset ID4D is visualized via an output unit (for example a screen). Alternatively, the four-dimensional image dataset ID4D may also be transferred to another system (for example to a "Picture Archiving and Communication System" ("PACS" for short)) or stored in a memory unit MU.

Figure 15:
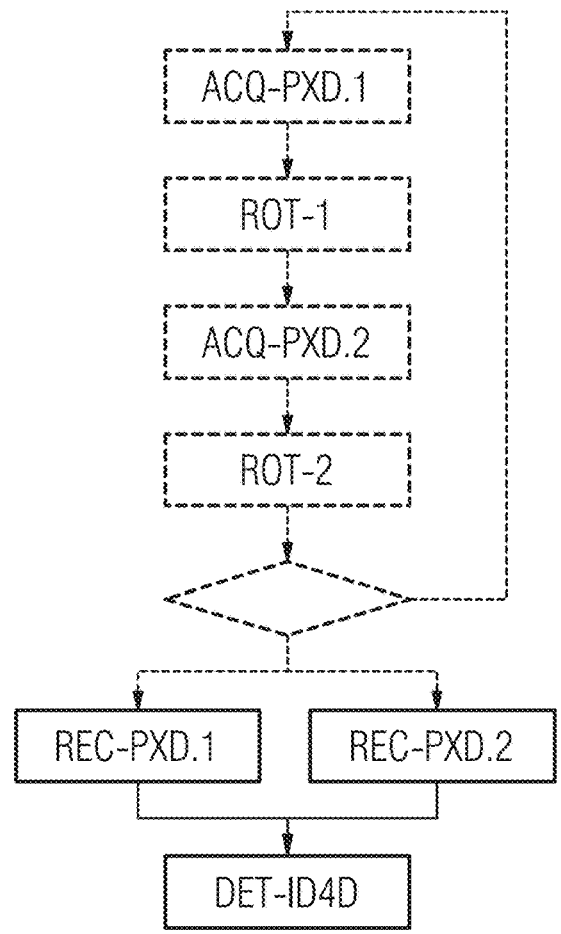
FIG. 15 shows a second example embodiment of a method for determining a four-dimensional image dataset of an examination volume.

FIG. 15 shows a second example embodiment of a method for determining a four-dimensional image dataset ID4D of an examination volume VOL.

The second example embodiment of the method may include all additional optional steps of the first example embodiment shown in FIG. 14. The individual steps of the second example embodiment may include the advantageous embodiments and developments described in relation to the first example embodiment.

The second example embodiment of the method additionally comprises the acquisition ACQ-XD.1 of one of the first X-ray datasets XD.1.1, . . . , XD.1.3 via a first X-ray source SRC.1 and a first X-ray detector DTC.1 of an X-ray device XSYS, and the acquisition ACQ-XD.2 of one of the second X-ray datasets XD.2.1, . . . , XD.2.2. In a first variant of the second example embodiment, the acquisition ACQ-XD.2 of one of the second X-ray datasets XD.2.1, . . . , XD.2.2 is accomplished via a second X-ray source SRC.2 and a second X-ray detector DTC.2 of the X-ray device. In a second variant of the second example embodiment, the acquisition ACQ-XD.2 of one of the second X-ray datasets XD.2.1, . . . , XD.2.2 is accomplished via the first X-ray source SRC.1 and the first X-ray detector DTC.1 of the X-ray device XSYS. In particular, the acquisition geometry of the first variant corresponds to the acquisition geometry shown in FIG. 12, and the acquisition geometry of the second variant corresponds to the acquisition geometry shown in FIG. 13.

In the first variant, the method optionally comprises in addition a first rotation ROT-1 of the X-ray sources SRC.1, SRC.2 and the X-ray detectors DTC.1, DTC.2 around the examination volume VOL, the first rotation ROT-1 usually taking place after the acquisition ACQ-XD.1 of one of the first X-ray datasets XD.1.1, . . . , XD.1.3 and before the acquisition ACQ-XD.2 of one of the second X-ray datasets XD.2.1, . . . , XD.2.2. In this second variant, the method additionally comprises a second rotation ROT-2 of the X-ray sources SRC.1, SRC.2 and the X-ray detectors DTC.1, DTC.2 around the examination volume VOL, the second rotation ROT-2 usually taking place before the acquisition ACQ-XD.1 of one of the first X-ray datasets XD.1.1, . . . , XD.1.3 and after the acquisition ACQ-XD.2 of one of the second X-ray datasets XD.2.1, . . . , XD.2.2.

In the second variant, the method optionally comprises in addition a first rotation ROT-1 of the first X-ray source SRC.1 and the first X-ray detector DTC.1 around the examination volume VOL, the first rotation ROT-1 usually taking place after the acquisition ACQ-XD.1 of one of the first X-ray datasets XD.1.1, . . . , XD.1.3 and before the acquisition ACQ-XD.2 of one of the second X-ray datasets XD.2.1, . . . , XD.2.2. In this second variant, the method additionally comprises a second rotation ROT-2 of the first X-ray source SRC.1 and the first X-ray detector DTC.1 around the examination volume VOL, the second rotation ROT-2 usually taking place before the acquisition ACQ-XD.1 of one of the first X-ray datasets XD.1.1, . . . , XD.1.3 and after the acquisition ACQ-XD.2 of one of the second X-ray datasets XD.2.1, . . . , XD.2.2.

In both variants, the first rotation ROT-1 and the second rotation ROT-2 may in particular be parts of a continuous rotational movement, in particular at a constant angular velocity. Thus, it is in particular not necessary for the rotation to be interrupted between the first rotation ROT-1 and the second rotation ROT-2.

The illustrated method steps of the acquisition ACQ-XD.1, ACQ-XD.2 and the rotation ROT-1, ROT-2 may in particular be repeated until a previously specified number of first X-ray datasets XD.1.1, . . . , XD.1.3 or second X-ray datasets XD.2.1, . . . , XD.2.3 have been acquired, or until a predefined angular range around the examination volume has been acquired. It is advantageous in particular to cover an angular range of greater than or equal to 180°, in particular an angular range greater than or equal to the sum of 180° and the aperture angle of the X-ray radiation used (typically 200°), with the X-ray datasets XD.1.1, . . . , XD.1.3, XD.2.1, . . . , XD.2.3 or, as the case may be, with the X-ray projections XP.1.1, . . . , XP.1.3, XP.2.1, . . . , XP.2.3.

After one of the illustrated abort criteria has been reached, the acquired X-ray datasets XD.1.1, . . . , XD.1.3, XD.2.1, . . . , XD.2.3 are transferred via the interface IF to the determination system DSYS. Alternatively. the X-ray datasets XD.1.1, . . . , XD.1.3, XD.2.1, . . . , XD.2.3 may also be transferred already during the acquisition of the remaining X-ray datasets XD.1.1, . . . , XD.1.3, XD.2.1, . . . , XD.2.3.

Figure 16:
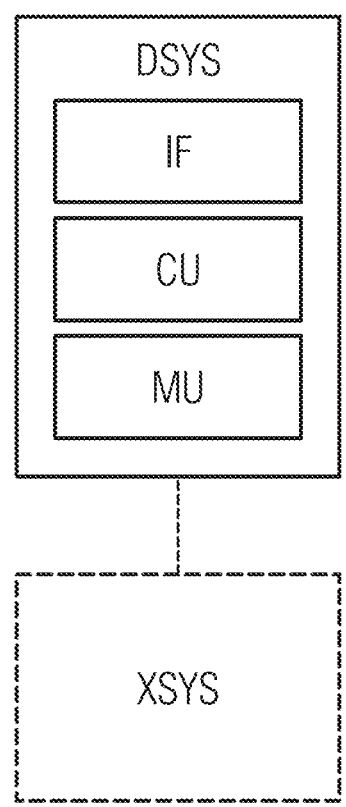
FIG. 16 shows a determination system.

FIG. 16 shows a determination system DSYS. The illustrated determination system DSYS is embodied for performing an inventive method for determining a three-dimensional image dataset ID.1, . . . , ID.5 or for determining a four-dimensional image dataset ID4D. The determination system DSYS comprises an interface IF, a computing unit CU and a memory unit MU.

The determination system DSYS may be in particular a computer, a microcontroller or an integrated circuit. Alternatively, the determination system DSYS may be a real or virtual network of computers (a common technical term used to describe a real network is "cluster", while a common technical term used to describe a virtual network is "cloud"). The determination system DSYS may also be embodied as a virtual system that is implemented on a real computer or a real or virtual network of computers (a common technical term used to describe this is "virtualization").

An interface IF may be a hardware or software interface (PCI bus, USB or FireWire, for example). A computing unit CU may include hardware elements or software elements, for example a microprocessor or a device known as an FPGA (acronym for "Field Programmable Gate Array"). A memory unit MU may be realized as a non-permanent working memory (Random Access Memory, or RAM for short) or as nonvolatile mass storage (hard disk, USB stick, SD card, solid-state disk).

The interface IF may in particular comprise a number of sub-interfaces which perform different steps of the respective methods. In other words, the interface IF may also comprise a plurality of interfaces IF. The computing unit CU may in particular comprise a number of sub-computing units which perform different steps of the respective methods. In other words, the computing unit CU may also be construed as a plurality of computing units CU.

Figure 17:
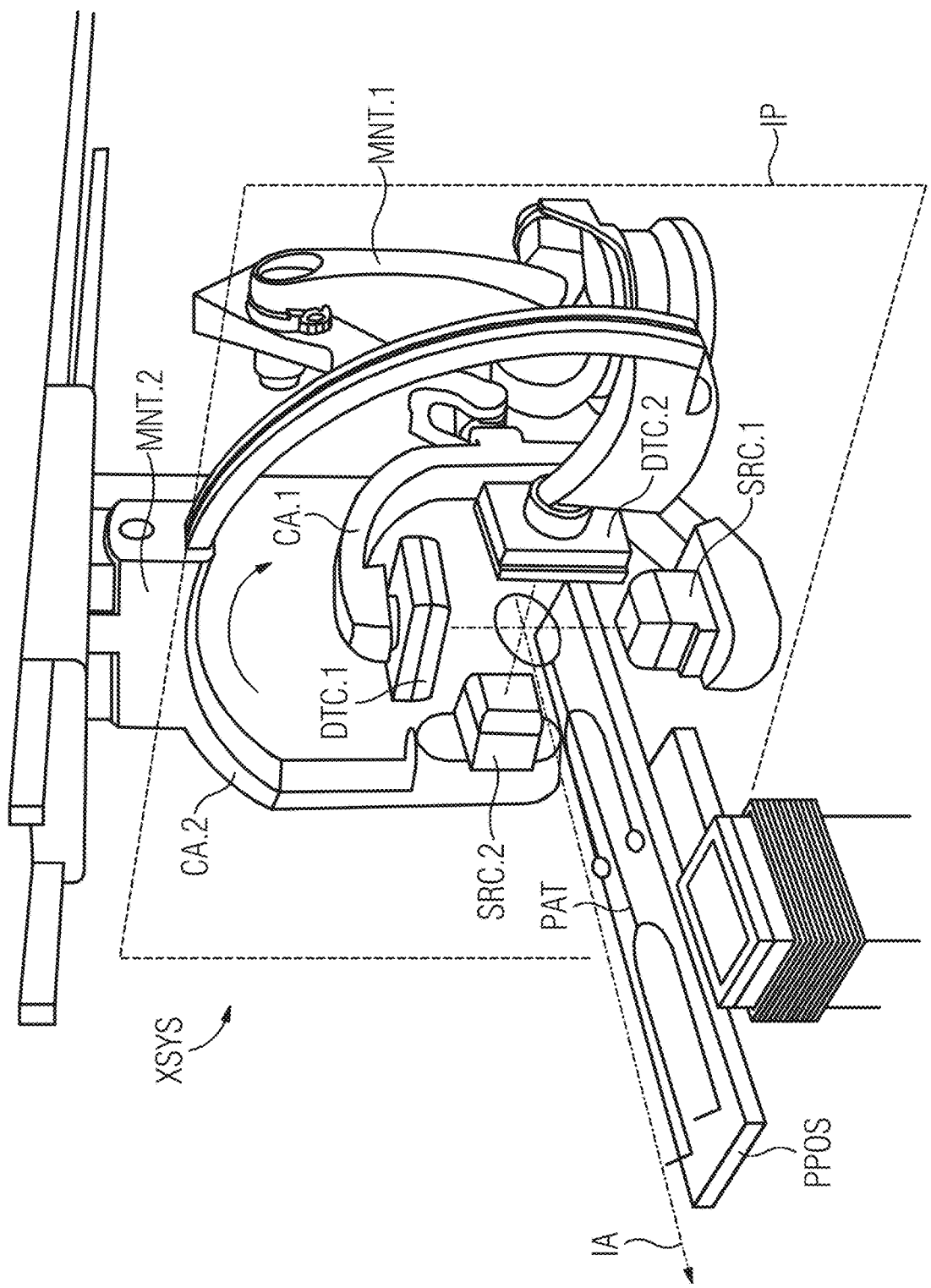
FIG. 17 shows an X-ray device.

FIG. 17 shows an example embodiment of an X-ray device XSYS. The X-ray device XSYS is embodied in this case as a double C-arm X-ray device. The X-ray device comprises a first C-arm CA.1, a first X-ray source SRC.1 being arranged at the first end of the first C-arm CA.1, and a first X-ray detector DTC.1 being arranged at the second end of the first C-arm CA.1. The X-ray device further comprises a second C-arm CA.2, a second X-ray source SRC.2 being arranged at the first end of the second C-arm CA.2, and a second X-ray detector being embodied at the second end of the second C-arm CA.2. The first C-arm CA.1 is arranged on a first mount MNT.1, the first mount being embodied as a multi-axis articulated robot. The second C-arm CA.2 is arranged on a second mount MNT.2, the second mount comprising a ceiling-mounted fixture.

The first X-ray source SRC.1 and the second X-ray source SRC.2 are each in particular an X-ray tube comprising in particular the same anode material. The first X-ray detector DTC.1 and the second X-ray detector are in particular flat-panel detectors.

In this example, the X-ray sources SRC.1, SRC.2 and the X-ray detectors DTC.1, DTC.2 are embodied to rotate around an imaging axis IA, in particular to rotate circularly around the imaging axis IA. In this case the imaging axis IA intersects in particular the examination volume VOL. When rotating around the imaging axis, the X-ray sources SRC.1, SRC.2 and the X-ray detectors move in an imaging plane IP, the imaging plane IP being arranged orthogonally to the imaging axis IA. The X-ray sources SRC.1, SRC.2 and the X-ray detectors DTC.1, DTC.2 are embodied in particular to rotate around the imaging axis IA in that the C-arms CA.1, CA.2 are embodied to rotate around the imaging axis IA.

The X-ray device XSYS further comprises a patient support and positioning device PPOS, the patient support and positioning device PPOS being embodied for supporting and positioning a patient PAT. In particular, the patient PAT can be moved along the imaging axis IA via the patient support and positioning device.

Where not yet explicitly realized, though beneficial and within the meaning of the invention, individual example embodiments and individual subordinate aspects or features thereof may be combined or interchanged with one another without leaving the scope of the present invention. Advantages of the invention that are described with reference to one example embodiment are also relevant, where applicable, to other example embodiments without being cited explicitly.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for determining a three-dimensional image dataset of an examination volume, comprising:
    receiving a first X-ray dataset of the examination volume, the first X-ray dataset including a two-dimensional first X-ray projection of the examination volume with respect to a first projection direction;
    receiving a second X-ray dataset of the examination volume, the second X-ray dataset including a two-dimensional second X-ray projection of the examination volume with respect to a second projection direction; and
    determining a first three-dimensional image dataset of the examination volume based on the two-dimensional first X-ray projection and the two-dimensional second X-ray projection.

2. The method of claim 1, wherein an angle between 45° and 135° exists between the first projection direction and the second projection direction.

3. The method of claim 2, wherein an angle between 60° and 120° exists between the first projection direction and the second projection direction.

4. The method of claim 3, wherein an angle between 85° and 95° exists between the first projection direction and the second projection direction.

5. The method of claim 1,
    wherein the first X-ray dataset includes a first time point, the first time point corresponding to a time point of an acquisition of the two-dimensional first X-ray projection,
    wherein the second X-ray dataset includes a second time point, the second time point corresponding to a time point of an acquisition of the two-dimensional second X-ray projection, and
    wherein a time interval between the first time point and the second time point is less than 5 s.

6. The method of claim 5, wherein the time interval between the first time point and the second time point is less than 2 s.

7. The method of claim 6, wherein the time interval between the first time point and the second time point is less than 0.02 s.

8. The method of claim 5, further comprising:
    determining a three-dimensional constraining image dataset of the examination volume, wherein the determining of the first three-dimensional image dataset is additionally based on the three-dimensional constraining image dataset.

9. The method of claim 8, wherein the determining of the three-dimensional constraining image dataset is based on the first X-ray dataset and the second X-ray dataset.

10. The method of claim 5, further comprising:
    acquiring the first X-ray dataset via a first X-ray source and a first X-ray detector of an X-ray device; and
    acquiring the second X-ray dataset via a second X-ray source and a second X-ray detector of the X-ray device.

11. The method of claim 5, further comprising:
    acquiring the first X-ray dataset via a first X-ray source and a first X-ray detector of an X-ray device, via a first rotation of the first X-ray detector and the first X-ray source around the examination volume; and
    acquiring the second X-ray dataset via the first X-ray source and the first X-ray detector of the X-ray device.

12. The method of claim 1, further comprising:
    receiving a third X-ray dataset of the examination volume, the third X-ray dataset including a two-dimensional third X-ray projection of the examination volume with respect to a third projection direction; and
    determining a second three-dimensional image dataset of the examination volume based on the two-dimensional second X-ray projection and the two-dimensional third X-ray projection.

13. The method of claim 12, wherein an angle of less than 45° exists between the first projection direction and the third projection direction.

14. The method of claim 13, wherein an angle of less than 300 exists between the first projection direction and the third projection direction.

15. The method of claim 14, wherein an angle of less than 5° exists between the first projection direction and the third projection direction.

16. The method of claim 12,
    wherein the second X-ray dataset includes a second time point, the second time point corresponding to a time point of an acquisition of the two-dimensional second X-ray projection,
    wherein the third X-ray dataset includes a third time point, the third time point corresponding to a time point of an acquisition of the two-dimensional third X-ray projection, and
    wherein a time interval between the second time point and the third time point is less than 5 s.

17. The method of claim 16, wherein the time interval between the second time point and the third time point is less than 2 s.

18. The method of claim 17, wherein the time interval between the second time point and the third time point is less than 0.02 s.

19. The method of claim 12, further comprising:
    determining a three-dimensional constraining image dataset of the examination volume, wherein the determining of the first three-dimensional image dataset is additionally based on the three-dimensional constraining image dataset.

20. The method of claim 19, wherein the determining of the three-dimensional constraining image dataset is based on the first X-ray dataset and the second X-ray dataset.

21. The method of claim 12, further comprising:
    acquiring the first X-ray dataset via a first X-ray source and a first X-ray detector of an X-ray device; and
    acquiring the second X-ray dataset via a second X-ray source and a second X-ray detector of the X-ray device.

22. The method of claim 12, further comprising:
    acquiring the first X-ray dataset via a first X-ray source and a first X-ray detector of an X-ray device, via a first rotation of the first X-ray detector and the first X-ray source around the examination volume; and acquiring the second X-ray dataset via the first X-ray source and the first X-ray detector of the X-ray device.

23. The method of claim 1, further comprising:
determining a three-dimensional constraining image dataset of the examination volume, wherein the determining of the first three-dimensional image dataset is additionally based on the three-dimensional constraining image dataset.

24. The method of claim 23, wherein the determining of the three-dimensional constraining image dataset is based on the first X-ray dataset and the second X-ray dataset.

25. The method of claim 23, further comprising:
determining a first three-dimensional back-projection dataset based on the first X-ray dataset and based on the three-dimensional constraining image dataset; and
determining a second three-dimensional back-projection dataset based on the second X-ray dataset and based on the three-dimensional constraining image dataset, wherein the first three-dimensional image dataset is based on the first three-dimensional back-projection dataset and is based on the second three-dimensional back-projection dataset.

26. The method of claim 25, wherein the determining of the first three-dimensional image dataset includes a multiplication of the first three-dimensional back-projection dataset with the second three-dimensional back-projection dataset.

27. The method of claim 1, further comprising:
acquiring the first X-ray dataset via a first X-ray source and a first X-ray detector of an X-ray device; and
acquiring the second X-ray dataset via a second X-ray source and a second X-ray detector of the X-ray device.

28. The method of claim 1, further comprising:
acquiring the first X-ray dataset via a first X-ray source and a first X-ray detector of an X-ray device, via a first rotation of the first X-ray detector and the first X-ray source around the examination volume; and
acquiring the second X-ray dataset via the first X-ray source and the first X-ray detector of the X-ray device.

29. A non-transitory computer program product storing a computer program, loadable into a memory of a determination system, the computer program including program sections for performing the method of claim 1 when the program sections are executed by the determination system.

30. A non-transitory computer-readable storage medium storing program sections, wherein the program sections, when executed by at least one processor, cause the at least one processor to perform the method of claim 1.

31. A determination system configured to determine a three-dimensional image dataset of an examination volume, the determination system comprising:
processing circuitry configured to
receive a first X-ray dataset of the examination volume, the first X-ray dataset including a two-dimensional first X-ray projection of the examination volume with respect to a first projection direction,
receive a second X-ray dataset of the examination volume, the second X-ray dataset including a two-dimensional second X-ray projection of the examination volume with respect to a second projection direction, and
determine a first three-dimensional image dataset of the examination volume based on the two-dimensional first X-ray projection and the two-dimensional second X-ray projection.

32. An X-ray device comprising the determination system of claim 31.

* * * * *